(12) United States Patent
East

(10) Patent No.: US 6,630,619 B1
(45) Date of Patent: Oct. 7, 2003

(54) **TOXIN GENES FROM THE BACTERIA *ENORHABDUS NEMATOPHILUS* AND *PHOTORHABDUS LUMINESCENS***

(75) Inventor: Peter David East, O'Connor (AU)

(73) Assignee: Commonwealth Scientific and Industrial Organisation, Campbell (AU)

( * ) Notice: Subject to any disclaimer, the term of this patent is extended or adjusted under 35 U.S.C. 154(b) by 0 days.

(21) Appl. No.: 09/463,048

(22) PCT Filed: Jul. 17, 1998

(86) PCT No.: PCT/AU98/00562

§ 371 (c)(1),
(2), (4) Date: Apr. 4, 2000

(87) PCT Pub. No.: WO99/03328

PCT Pub. Date: Jan. 28, 1999

(30) Foreign Application Priority Data

Jul. 17, 1997 (AU) ............................................. PO 8088

(51) Int. Cl.[7] ............................ A01H 5/00; C12N 1/21; C12N 1/19; C12N 1/11; C12N 5/04; C12N 15/31; C12N 15/82; C12P 21/02

(52) U.S. Cl. ........................ 800/302; 800/279; 800/288; 536/23.7; 435/468; 435/418; 435/419; 435/252.3; 435/255.1; 435/258.1; 435/71.1

(58) Field of Search ...................... 536/23.7; 435/252.3, 435/254.2, 255.1, 258.1, 418, 468, 71.1, 71.2, 71.3, 419; 800/279, 302, 288

(56) References Cited

U.S. PATENT DOCUMENTS 5,972,687 A * 10/1999 Smigielski et al.

FOREIGN PATENT DOCUMENTS

| WO | 0142924 | * | 9/1984 |
|---|---|---|---|
| WO | WO 95/00647 | | 1/1995 |
| WO | 95/00647 | | 1/1995 |
| WO | wo95/00647 | * | 1/1995 |
| WO | WO 97/17432 | | 5/1997 |

OTHER PUBLICATIONS

Jouanin et al. Transgenic plants for insect resistance Plant Science 131 1998 1–11.*
Smigocki et al. cytokinin–mediated insect resistance in Nicotiana plants transformed with the ipt gene 23: 325–335 1993.*
Pang et al. Expression of a gene encoding a scorpion insectotoxin peptide in yeast, bacteria and plants Gene 116 1992 165–172.*
Broun et al. Catalytic plasticity of fatty acid modification enzymes underlying chemical diversityy of plant lipids Science vol. 282 Nov. 13, 1998.*
Lazar et al. Transforming growth factor a: mutation of aspartic acid 47 and leucine 48 resultd in different biological activites Mar. 1988 p. 1247–1252 vol. 8, No. 3.*
Bowie et al. Deciphering the message in protein sequences: tolerance to amino acid substitutions Science, vol. 247.*
Hongsthong et al: "Optimum conditions for insecticidal toxin production by Photorhabdus luminescens" Abstracts of the General Meeting of the American Society for Microbiology, The Society, Washington, DC, US, No. 95, May 1, 1995, pp. 408–AbstrQ–48, XP002076055 ISSN: 1060–2011.
Bowen DJ et al: "Extracellular Insecticidal Factor Produced by Xenorhabdus luminescens" Abstracts of the Annual Meeting of the American Society for Microbiology, Washington, DC, US, vol. 90, 1989, p. 228 XP002119858 ISSN: 0094–8519.
Clarke David J et al:Virulence mechanisms of Photorhabdus sp. strain K122 toward wax moth larvae. Journal of Invertebrate Pathology, vol. 66, No. 2, 1995, pp. 149–155, XP001064286 ISSN: 0022–2011.
Hu, k. et al.: "Mortality of Plant–Parasitic Nematodes Caused by Bacterial (Xenorhabdus SPP. and Photorhabdus Luminescens) Culture Media" Journal of Nematology, Society of Nematologists, College Park, MD, US, vol. 27, No. 4, 1995, pp. 502–503, XP000905673 ISSN: 0022–300X.
David Joseph Bowen: "Characterization of a High Molecular Weight Insecticidal Protein Complex Produced by the Entomopathogenic bacterium Photorhabdus luminescens (Nematodes, Biological Control)" Thesis Universidty Wisconsin, XX, XX, May 1, 1995, XP002076022.
B. Brunel et al., Fast and Accurate Identification of *Xenorhabdus* and *Photorhabdus* Species by Restriction Analysis of PCR–Amplified 16S rRNA Genes, Applied and Environmental Microbiology, vol. 63, Feb. 1997, pp. 574–580.
S. Henikoff, Unidirectional Digestion with Exonuclease III Creates Targeted Breakpoints for DNA Sequencing, Gene, vol. 28, 1984, pp. 351–359.
M. A. Innis et al., PCR Protocols: A Guide to Methods and Applications, Academic Press, Inc. 1990, pp. 3–20.
J. Marmur, A Procedure for the Isolation of Deoxyribonucleic Acid from Micro–organisms, J. Mol. Biol., vol. 3, 1961, pp. 208–218.
K.F. Scott et al., Biological Nitrogen Fixation: Primary Structure of the *Klebsiella Pneumoniae* nifH and nifD Genes, Journal of Molecular and Applied Genetics, vol. 1, pp. 71–81.

* cited by examiner

*Primary Examiner*—David T. Fox
*Assistant Examiner*—Anne Kubelik
(74) *Attorney, Agent, or Firm*—McDermott, Will & Emery

(57) ABSTRACT

The invention relates to the identification and isolation of polynucleotide molecules encoding a new class of protein insecticidal toxins which are produced by bacteria from the genera Xenorhabdus and Photorhabdus. The polynucleotide molecules may be incorporated into, for example, insect-specific viruses (including entomopox and nuclear polyhedrosis viruses), bacteria (including Gracilicutes, Firmicutes, Tenericutes and Mendosicutes), protozoa, yeast and plants for control of pest insects.

5 Claims, 9 Drawing Sheets

Figure 3:
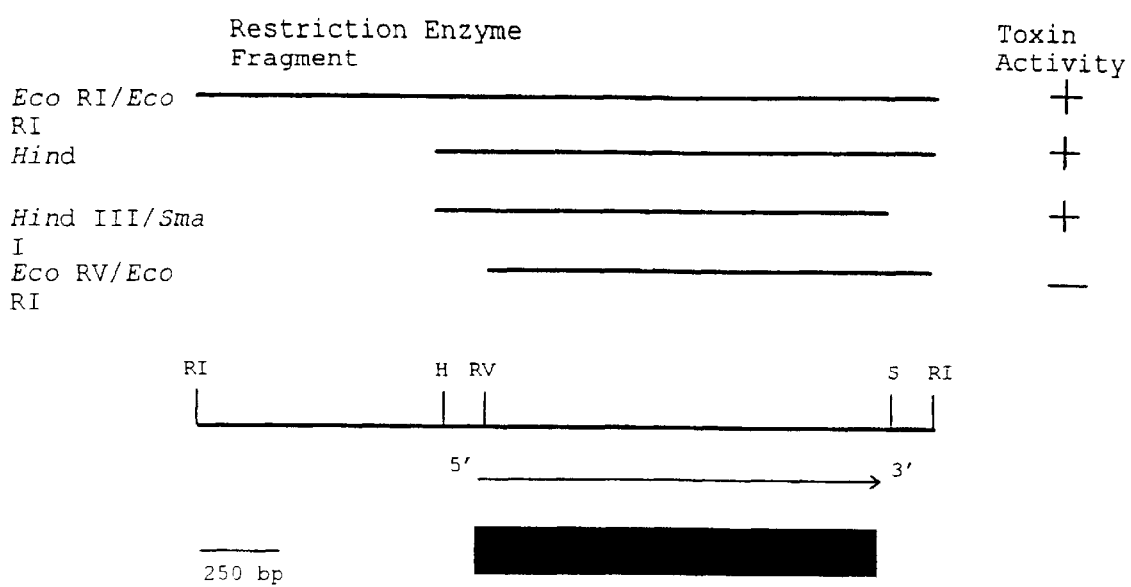

```
   1 ATAATGGGAA AGTACAATGG TTATTAAACC CGTAACAACT CCGAGTGTAA
  51 TACAATTAAC GCCTGATGAT AGAGTAACGC CTGATGATAA AGGTGAATAT
 101 CAACCCGTTG AAAAGCAAAT AGCGGGAGAT ATAATACGTG TACTAGAATT
 151 CAAGCAAACA AATGAAAGTC ATACAGGATT GTATGGAATT GCATATCGAG
                                             TOX F2
 201 CTAAGAAAGT AATAATAGCA TATGCTTTAG CGGTAAGTGG TATTCATAAT
 251 GTCTCTCAAC TTCCAGAAGA CTATTATAAA AATAAGGATA ACACAGGTAG
 301 AATTTATCAA GAATACATGT CTAATCTTTT ATCTGCACTA TTGGGTGAGA
 351 ATGGTGATCA AATTTCTAAA GATATGGCAA ATGATTTTAC CCAGAACGAA
 401 CTGGAGTTTG GAGGTCAACG TCTTAAAAAT ACCTGGGATA TTCCTGATCT
 451 TGAGAATAAA CTATTGGAAG ATTATTCAGA TGAAGATAAA TTATTAGCAC
                                                TOX F1
 501 TATATTTCTT TGCTTCACAA GAACTTCCAA TGGAGGCAAA TCAACAATCA
                                              TOX R3
 551 AATGCAGCAA ATTTTTTTAA AGTAATTGAT TTTTTACTTA TCTTATCTGC
 601 TGTAACATCA CTGGGAAAAA GGATTTTTTC AAAAAATTTT TACAATGGTC
 651 TAGAAACTAA ATCATTAGAG AATTATATTG AGAGAAAAAA ACTTTCTAAA
                                           TOX F3
 701 CCTTTCTTTC GACCACCGCA GAAGTTACCT GATGGCAGAA CAGGCTACTT
 751 GGCCGGTCCA ACAAAAGCGC CTAAATTGCC AACAACGTCT TCTACAGCAA
                                                  TOX R4
 801 CAACGTCTAC AGCAGCTTCA TCTAATTGGA GAGTTAGTTT GCAAAAACTT
 851 AGAGATAACC CATCCAGAAA TACATTTATG AAAATGGATG ATGCTGCAAA
 901 ACGAAAATAT AGTTCATTTA TAAAGAGGT ACAAAAGGGT AATGATCCAC
 951 GTGCAGCAGC AGCAAGTATT GGTACAAAAA GCGGCAGTAA CTTCGAAAAA
1001 CTGCAAGGTA GAGATTTATA TAGTATAAGA CTAAGCCAAG AACACAGGGT
                                             A24AC1
1051 AACATTCTCC ATAAATAATA CTGACCAAAT AATGGAGATC CAAAGTGTTG
1101 GAACTCATTA CCAAAATATA TAACCTGATT TATAGTAGTG ATAAGACGTA
1151 AGATAAATAT GGAAGGTTGT AATTCTATTG CACTTCCTCA GAGGTGACCG
1201 CTCAG
```

FIGURE 1.

```
  1  MVIKPVTTPS  VIQLTPDDRV  TPDDKGEYQP  VEKQIAGDII  RVLEFKQTNE
 51  SHTGLYGIAY  RAKKVIIAYA  LAVSGIHNVS  QLPEDYYKNK  DNTGRIYQEY
101  MSNLLSALLG  ENGDQISKDM  ANDFTQNELE  FGGQRLKNTW  DIPDLENKLL
151  EDYSDEDKLL  ALYFFASQEL  PMEANQQSNA  ANFFKVIDFL  LILSAVTSLG
201  KRIFSKNFYN  GLETKSLENY  IERKKLSKPF  FRPPQKLPDG  RTGYLAGPTK
251  APKLPTTSST  ATTSTAASSN  WRVSLQKLRD  NPSRNTFMKM  DDAAKRKYSS
301  FIKEVQKGND  PRAAAASIGT  KSGSNFEKLQ  GRDLYSIRLS  QEHRVTFSIN
351  NTDQIMEIQS  VGTHYQNI
```

FIGURE 2

```
   1 AAGCTTGCTA ATAATTCTTG CGTAAGTTAA TTTTACATTG AAATTAACGC
     ‾‾‾‾‾‾
     Hind III
  51 TTAAAAGCC  AGGGAAAACT CTATATTTAA AGTTGAAATT TATATTAGTA
 101 GCGACAAATT GCGGAGTTTT CTGCCAGAAA TTTCATAGCT CAAATAAACA
 151 TTAACATAAT GGAGAAATAT AATGGTTATA CAATTAACAC CTGATGATAG
 201 AAGTGGATAT CCACCCGTTG AAAAGCAAAT AGCAGGAGAT ATAGTACGTA
            ‾‾‾‾‾‾
            Eco RV
 251 TACTAAACTT TAAGCAAACA GATGAGGGTC ATACAGCATC ATATGGAATT
 301 GAATATCGAG CTAAGAAAAT AATATTAGCT TACGCTTTGG CTGTAAGTGG
                                     ←‾‾‾‾‾‾‾‾‾‾‾‾‾‾‾‾‾‾
                                                 AC4R
 351 TATTCATAAT GTATCTAAAC TTCCTGATGA CTATTATAAG AATAAAGAGA
 401 CTGCTGAGAG AATTTATCAA GAATATATGT CTAATCTTTC ATCTGCACTA
 451 TTAGGTGAAA ATGGTGATCA AATTTCTAAA GATATGGCAA ATGGTTTTA
                   AC2F
 501 TAAGAATGAA CTGGATTTTG AAGGTCAATA TCCTCAAAAC ATTTGGAATG
                          ‾‾‾‾‾‾‾‾‾‾‾‾‾‾‾‾‾‾‾‾→
 551 TTCCTGAGCT TGAAAATAAA CCATTGAGTG CTTATTCAGA TGACGATAAA
                                    ←‾‾‾‾‾‾‾‾‾‾‾‾‾‾‾‾‾‾‾
                                              AC7R
 601 TTATTAGCAC TATATTTTTT CTCTGTACAG GAAATTCCAC TGGAGGAAAA
 651 TCAACAATCA AATGCCGCAA GATTTTTTAA ATTAATTGAT TTCTTATTTA
 701 CCTTATCTGC TGTAACTTCA CTGGGAAGGA GGATTTTTTC AAAAAACTTT
 751 TACAATGGAT TAGAGGCTAA ATCATTAGAG AATTATATTG AGAGAAAAAA
                        AC6F
 801 ACTTTCTAAA CCTTTCTTTC GACCACCGCA GAGATTACCT GATGGCAGAA
         ‾‾‾‾‾‾‾‾‾‾‾‾‾‾‾‾‾‾‾‾‾‾‾‾‾‾‾‾‾‾→
 851 TAGGTTATTT GGCTGGACCA ACAGAAGCGC CTAAATGGAG AGTGAGTTTT
                        ←‾‾‾‾‾‾‾‾‾‾‾‾‾‾‾‾‾‾‾‾
                                 AC5R
 901 AAAGAACTTA AAAATAACAA ATCTAGGAAT GGATTTTCTA ATATGGAAGG
 951 GGCTGCAAAA CAAAAGTATA GTTCATTTAT AAAAGAGGTA CAAAAGGGTA
1001 ACGCTCCACA GACAGCAGCG AAAAGTATTG GTACAGCCAG TGGCAGTAAC
1051 CTGGAAAAAT TGCCGAATAA TTTATATAGT GTGAGGCTAA GCCAAAAAGA
                                                    AC3F
1101 CAGGGTAACC TTTACTCAAA ATGATACTGA CAATACAATG ACGGTTCATA
                                              ‾‾‾‾‾‾‾‾‾‾‾‾
                                                     AC8R
1151 GTGTTGGAAC TCATTATAAA AATATATGAT GAGTAATCTC TGACTTCGAT
     ‾‾‾‾‾‾‾‾‾→
1201 TGACAGAGCA TTTTTAAGCT CTCATTTTCT CAACGGGAGT CTCATAAGGC
1251 GTTTTACTTT TCAAGCCACT ATGTGGTCTG TGATAATTGT AAAACGCCTT
1301 CTTTTAGCCA ATACACTTTA CTACCAAGAA AATATATACC CTATGGATTT
     ←‾‾‾‾‾‾‾‾‾‾‾‾‾‾‾‾‾‾‾‾‾‾‾‾‾‾‾‾‾‾‾‾‾‾‾‾‾‾‾
                  V16AC1
1351 CAAGATGGAT CGCGGCGGCA AGGGAGCGAA TCCCCGGG
                                        ‾‾‾‾‾
                                        Sma I
```

FIGURE 4

```
  1  MVIQLTPDDR SGYPPVEKQI AGDIVRILNF KQTDEGHTAS YGIEYRAKKI
 51  ILAYALAVSG IHNVSKLPDD YYKNKETAER IYQEYMSNLS SALLGENGDQ
101  ISKDMANGFY KNELDFEGQY PQNIWNVPEL ENKPLSAYSD DDKLLALYFF
151  SVQEIPLEEN QQSNAARFFK LIDFLFTLSA VTSLGRRIFS KNFYNGLEAK
201  SLENYIERKK LSKPFFRPPQ RLPDGRIGYL AGPTEAPKWR VSFKELKNNK
251  SRNGFSNMEG AAKQKYSSFI KEVQKGNAPQ TAAKSIGTAS GSNLEKLPNN
301  LYSVRLSQKD RVTFTQNDTD NTMTVHSVGT HYKNI
```

FIGURE 5

```
 17  ATGGTTATTAAACCCGTAACAACTCCGAGTGTAATACAATTAACGCCTGA  66
                                                      |
172  .................................................ATGGT 176

67  TGATAGAGTAACGCCTGATGATAAAGGTGAATATCAACCCGTTGAAAAGC 116
     |    | ||||  |||||||||| | |||  |||||  ||||||||||||
177  TATACAATTAACACCTGATGATAGAAGTGGATATCCACCCGTTGAAAAGC 226

117  AAATAGCGGGAGATATAATACGTGTACTAGAATTCAAGCAAACAAATGAA 166
     |||||||   |||||||| ||||| ||||| | ||  ||||||||| |||
227  AAATAGCAGGAGATATAGTACGTATACTAAACTTTAAGCAAACAGATGAG 276

167  AGTCATACAGGATTGTATGGAATTGCATATCGAGCTAAGAAAGTAATAAT 216
     ||||||||| ||  ||||||||||  ||||||||||||||||| ||||| |
277  GGTCATACAGCATCATATGGAATTGAATATCGAGCTAAGAAAATAATATT 326

217  AGCATATGCTTTAGCGGTAAGTGGTATTCATAATGTCTCTCAACTTCCAG 266
     ||| || ||||| || ||||||||||||||||||||| ||| |||||| |
327  AGCTTACGCTTTGGCTGTAAGTGGTATTCATAATGTATCTAAACTTCCTG 376

267  AAGACTATTATAAAAATAAGGATAACACAGGTAGAATTTATCAAGAATAC 316
     | ||||||||||  |||| ||  |  |  | ||||||||||||||||||
377  ATGACTATTATAAGAATAAAGAGACTGCTGAGAGAATTTATCAAGAATAT 426

317  ATGTCTAATCTTTTATCTGCACTATTGGGTGAGAATGGTGATCAAATTTC 366
     ||||||||||||| |||||||||||| |||||  ||||||||||||||||
427  ATGTCTAATCTTTCATCTGCACTATTAGGTGAAAATGGTGATCAAATTTC 476

367  TAAAGATATGGCAAATGATTTTACCCAGAACGAACTGGAGTTTGGAGGTC 416
     ||||||||||||||||| ||||    |||| |||||||| ||| |||||
477  TAAAGATATGGCAAATGGTTTTATAAGAATGAACTGGATTTTGAAGGTC 526

417  AACGTCTTAAAAATACCTGGGATATTCCTGATCTTGAGAATAAACTATTG 466
     ||  || | |||| |  |||  |||||| |||||||||||| ||| ||||
527  AATATCCTCAAAACATTTGGAATGTTCCTGAGCTTGAAAATAAACCATTG 576

467  GAAGATTATTCAGATGAAGATAAATTATTAGCACTATATTTCTTTGCTTC 516
      ||||||||||||||| ||||||||||||||||||||||||  ||  ||
577  AGTGCTTATTCAGATGACGATAAATTATTAGCACTATATTTTTCTCTGT 626

517  ACAAGAACTTCCAATGGAGGCAAATCAACAATCAAATGCAGCAAATTTTT 566
     ||| ||| || ||| |||||| |||||||||||||||||| ||| ||||
627  ACAGGAAATTCCACTGGAGGAAAATCAACAATCAAATGCCGCAAGATTTT 676
```

FIGURE 6A

```
567  TTAAAGTAATTGATTTTTTACTTATCTTATCTGCTGTAACATCACTGGGA  616
     |||||  ||||||||||| |||  |||  |||||||||||||||  |||||||||
677  TTAAATTAATTGATTTCTTATTTACCTTATCTGCTGTAACTTCACTGGGA  726

617  AAAAGGATTTTTTCAAAAAATTTTTACAATGGTCTAGAAACTAAATCATT  666
     |    |||||||||||||||||| ||||||||||  ||||    |||||||||
727  AGGAGGATTTTTTCAAAAAACTTTTACAATGGATTAGAGGCTAAATCATT  776

667  AGAGAATTATATTGAGAGAAAAAAACTTTCTAAACCTTTCTTTCGACCAC  716
     |||||||||||||||||||'|||||||||||||||||||||||||||||
777  AGAGAATTATATTGAGAGAAAAAAACTTTCTAAACCTTTCTTTCGACCAC  826

717  CGCAGAAGTTACCTGATGGCAGAACAGGCTACTTGGCCGGTCCAACAAAA  766
     ||||||  |||||||||||||||||| ||| || ||||| || ||||||| ||
827  CGCAGAGATTACCTGATGGCAGAATAGGTTATTTGGCTGGACCAACAGAA  876

767  GCGCCTAAATTGCCAACAACGTCTTCTACAGCAACAACGTCTACAGCAGC  816
     ||||||||
877  GCGCCTAAA...................................  885

817  TTCATCTAATTGGAGAGTTAGTTTGCAAAAACTTAGAGATAACCCATCCA  866
                  |||||||| |||| || |||||| | ||||| ||| |
886  ..........TGGAGAGTGAGTTTTAAAGAACTTAAAAATAACAAATCTA  925

867  GAAATACATTTATGAAAATGGATGATGCTGCAAAACGAAAATATAGTTCA  916
     | ||| ||||   || ||||| | ||||||||| ||| |||||||||
926  GGAATGGATTTTCTAATATGGAAGGGGCTGCAAAACAAAAGTATAGTTCA  975

917  TTTATAAAGAGGTACAAAAGGGTAATGATCCACGTGCAGCAGCAGCAAG  966
     ||||||||||||||||||||||||||| | ||||| |||||||  |||
976  TTTATAAAGAGGTACAAAAGGGTAACGCTCCACAGACAGCAGCGAAAAG  1025

967  TATTGGTACAAAAAGCGGCAGTAACTTCGAAAAACTGCAAGGTAGAGATT  1016
     |||||||||   || |||||||||| |||||||| |||    ||   |||
1026 TATTGGTACAGCCAGTGGCAGTAACCTGGAAAAATTGCCGAATA...ATT  1072

1017 TATATAGTATAAGACTAAGCCAAGAACACAGGGTAACATTCTCCATAAAT  1066
     |||||||| |  || |||||||||| |||||||||| ||  |   ||||
1073 TATATAGTGTGAGGCTAAGCCAAAAAGACAGGGTAACCTTTACTCAAAAT  1122

1067 AATACTGACCAAATAATGGAGATCCAAAGTGTTGGAACTCATTACCAAAA  1116
     ||||||||  || ||||  | || ||||||||||||||||||||  ||||
1123 GATACTGACAATACAATGACGGTTCATAGTGTTGGAACTCATTATAAAAA  1172

1117 TATATAA[...] 1123 [0]
     ||||‾‾‾
1173 TATATGA 1179
```

```
  1 MVIKPVTTPSVIQLTPDDRVTPDDKGEYQPVEKQIAGDIIRVLEFKQTNE 50
            |||||||||        ::|.||||||||||:|:|:||||:|
  1 .........MVIQLTPDDR......SGYPPVEKQIAGDIVRILNFKQTDE 35

51 SHTGLYGIAYRAKKVIIAYALAVSGIHNVSQLPEDYYKNKDNTGRIYQEY 100
    :||:  |||.|||||:|:||||||||||||.||:|||||||:...||||||
 36 GHTASYGIEYRAKKIILAYALAVSGIHNVSKLPDDYYKNKETAERIYQEY 85

101 MSNLLSALLGENGDQISKDMANDFTQNELEFGGQRLKNTWDIPDLENKLL 150
    ||||  ||||||||||||||||:|  .|||:|:||   .|.|::|:||||  |
 86 MSNLSSALLGENGDQISKDMANGFYKNELDFEGQYPQNIWNVPELENKPL 135

151 EDYSDEDKLLALYFFASQELPMEANQQSNAANFFKVIDFLLILSAVTSLG 200
    ..|||:||||||||||.  ||:|:|.|||||||.|||:||||:.||||||||
136 SAYSDDDKLLALYFFSVQEIPLEENQQSNAARFFKLIDFLFTLSAVTSLG 185

201 KRIFSKNFYNGLETKSLENYIERKKLSKPFFRPPQKLPDGRTGYLAGPTK 250
    :|||||||||||.|||||||||||||||||||||||:|||||.|||||||.
186 RRIFSKNFYNGLEAKSLENYIERKKLSKPFFRPPQRLPDGRIGYLAGPTE 235

251 APKLPTTSSTATTSTAASSNWRVSLQKLRDNPSRNTFMKMDDAAKRKYSS 300
    |||                  ||||:..|::|.|||.| .|::|||.||||
236 APK................WRVSFKELKNNKSRNGFSNMEGAAKQKYSS 268

301 FIKEVQKGNDPRAAAASIGTKSGSNFEKLQGRDLYSIRLSQEHRVTFSIN 350
    ||||||||.|..|| |||| ||||:|||.. :|||:||||..||||. |
269 FIKEVQKGNAPQTAAKSIGTASGSNLEKLPN.NLYSVRLSQKDRVTFTQN 317

351 NTDQIMEIQSVGTHYQNI 368
    :||..|.::|||||||.||
318 DTDNTMTVHSVGTHYKNI 335
```

FIGURE 7

TOXIN GENES FROM THE BACTERIA *XENORHABDUS NEMATOPHILUS* AND *PHOTORHABDUS LUMINESCENS*

FIELD OF THE INVENTION

The present invention concerns the identification and isolation of a new class of protein toxins with specificity for insects, which are produced by bacteria from the genera Xenorhabdus and Photorhabdus. In addition, the present invention relates to the incorporation of genes encoding this class of toxin into, for example, insect-specific viruses (including entomopox and nuclear polyhedrosis viruses), bacteria (including Gracilicutes, Firmicutes, Tenericutes and Mendosicutes), yeast and plants for control of insect pests.

BACKGROUND OF THE INVENTION

Insect pathogenic nematodes of the families Steinernematidae and Heterorhabditidae are known to be symbiotically associated with bacteria of the genera Xenorhabdus and Photorhabdus respectively. It has been observed that these bacteria have the ability to kill a wide range of different insects without the aid of their nematode partners. The present inventors have isolated polynucleotide molecules encoding a new class of protein insecticidal toxins from *Xenorhabdus nematophilus* strain A24 and *Photorhabdus luminescens* strain V16/1.

DISCLOSURE OF THE INVENTION

In a first aspect, the present invention provides an isolated polynucleotide molecule encoding an insecticidal toxin, said polynucleotide molecule comprising a nucleotide sequence which substantially corresponds to the nucleotide sequence shown as SEQ ID NO: 1 or SEQ ID NO: 2.

In a second aspect, the present invention provides an isolated polynucleotide molecule encoding an insecticidal toxin, said polynucleotide molecule comprising a nucleotide sequence having at least 85%, more preferably at least 95%, sequence identity to the nucleotide sequence shown as SEQ ID NO: 2.

In a third aspect, the present invention provides an insecticidal toxin, in a substantially pure form, which toxin comprises an amino acid sequence having at least 95% sequence identity to that shown as SEQ ID NO: 3.

In a fourth aspect, the present invention provides an insecticidal toxin, in a substantially pure form, which toxin comprises an amino acid sequence having at least 85%, more preferably at least 95%, sequence identity to that shown as SEQ ID NO: 4.

Most preferably, the insecticidal toxin of the third or fourth aspect comprises an amino acid sequence substantially corresponding to that shown as SEQ ID NO: 3 or SEQ ID NO: 4 respectively.

In a fifth aspect the present invention provides a recombinant microorganism, the recombinant microorganism being characterised in that it is transformed with and expresses the polynucleotide molecule of the first or second aspects of the present invention.

The microorganisms which may be usefully transformed with the polynucleotide molecule of the first or second aspects of the present invention include bacteria, such as Escherichia, Gracilicutes, Firmicutes, Tenericutes and Mendosicutes; protozoa and yeast. The microorganism can be transformed by routine methods using expression vectors comprising the toxin-encoding polynucleotide molecule operably linked to a suitable inducible or constitutive promoter sequence.

In a sixth aspect, the present invention provides a method of producing an insecticidal toxin, said method comprising:
(i) culturing a microorganism according to the fourth aspect under conditions suitable for the expression of the toxin-encoding polynucleotide molecule, and
(ii) optionally recovering the expressed insecticidal toxin.

In a seventh aspect, the present invention provides a recombinant insect-specific virus, the recombinant insect-specific virus being characterised in that it includes within a non-essential region of its genome the polynucleotide molecule of the first or second aspects of the present invention operably linked to a suitable inducible or constitutive promoter sequence.

The recombinant insect-specific virus of the seventh aspect is preferably selected from entomopox and nuclear polyhedrosis viruses. The recombinant virus can be produced by routine methods such as homologous recombination.

In an eighth aspect, the present invention provides a method for killing pest insects, said method comprising applying to an area infested with said insects an effective amount of a recombinant microorganism according to the fourth aspect and/or a recombinant virus according to the seventh aspect, optionally in admixture with an acceptable agricultural carrier.

In a ninth aspect, the present invention provides a plant transformed with, and capable of expressing, the polynucleotide molecule of the first or second aspects of the present invention.

The plant according to the ninth aspect may be any plant of agricultural, arboricultural, horticultural or ornamental value that is susceptible to damage by feeding pest insects. However, preferably, the plant is selected from plants of agricultural value such as cereals (e.g.; wheat and barley), vegetable plants (e.g.; tomato and potato) and fruit trees (e.g., citrus trees and apples). Other preferred plants include tobacco and cotton.

The plant can be transformed by routine methods including Agrobacterium transformation and electroporation. Preferably, the toxin-encoding polynucleotide molecule is operably linked to a suitable inducible or constitutive promoter sequence. Particularly preferred promoter sequences include the cauliflower mosaic virus (CaMV 35 S) promoter element and promoter elements from the sub-clover stunt virus (SCSV).

The term "substantially corresponds" as used herein in relation to the nucleotide sequence is intended to encompass minor variations in the nucleotide sequence which due to degeneracy do not result in a change in the encoded protein. Further this term is intended to encompass other minor variations in the sequence which may be required to enhance expression in a particular system but in which the variations do not result in a decrease in biological activity of the encoded protein.

The term "substantially corresponding" as used herein in relation to the amino acid sequence is intended to encompass minor variations in the amino acid sequence which do not result in a decrease in biological activity of the insecticidal toxin. These variations may include conservative amino acid substitutions. The substitutions envisaged are:

G, A, V, I, L, M; D, E; N, Q; S, T; K, R, H; F, Y, W, H; and P. Nα-alkalamino acids.

The term "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by way of reference to the following, non-limiting example and accompanying figures.

BRIEF DESCRIPTION OF THE ACCOMPANYING FIGURES

FIG. 1: Nucleotide sequence of the protein coding (sense) strand of the *X. nematophilus* DNA insert of clone toxb4 (SEQ ID NO: 5). The translation initiation codon (ATG) at nucleotide position 17–19 and the translation termination codon (TAA) at nucleotide position 1121–1123 are indicated by shaded boxes. Locations of oligonucleotide sequences used for sequencing primer design are indicated by arrow and a primer name (TOX F2 (SEQ ID NO: 7), TOX F1 (SEQ ID NO:8), TOX R3 (SEQ ID NO:9), TOX F3 (SEQ ID NO:10), TOX R4 (SEQ ID NO:11), A24AC1 (SEQ ID NO:12)). Arrows directed left-to-right, positioned above the sequence indicate sense-strand primers, arrows directed right-to-left, positioned below the sequence indicate anti-sense primers.

FIG. 2: Deduced sequence of the 368 amino acid toxb4 protein from *X. nematophilus* strain A24, derived by conceptual translation of the long open reading frame commencing at nucleotide position 17 and ending at nucleotide position 1120 of the toxb4 gene sequence (FIG. 1) (SEQ ID NO:3).

FIG. 3: Restriction map of *P. luminescens* V16/1 toxin gene clone showing location of putative toxin protein coding region (solid black box) and direction of transcription (arrow). RI=EcoRI, RV=EcoRV, H=Hind III, S=Sma I. Toxin production from clones containing selected restriction fragments is indicated above the restriction map (+, toxin activity; –, no toxin activity).

FIG. 4: Nucleotide sequence of the protein coding (sense) strand of the *P. luminescens* Hind III/Sma I DNA fragment (SEQ ID NO:6). Translation initiation (ATG) and termination (TGA) codons are indicated by shaded boxes. Locations of oligonucleotide sequences used for sequencing primer design are indicated by arrows and a primer name as described in the brief description of FIG. 1 (AC4R (SEQ ID NO:13), AC2F (SEQ ID NO:14), AC7R (SEQ ID NO:15), AC6F (SEQ ID NO:16), AC5R (SEQ ID NO:17), AC3F (SEQ ID NO:18), AC8R (SEQ ID NO:19), and V16AC1 (SEQ ID NO:20)). Restriction enzyme sites used for sub-cloning and identification of sequences necessary for toxin activity are underlined and labelled on the figure.

FIG. 5: Deduced sequence of the 335 amino acid PlV16tox1 protein from *P. luminescens* strain V16/1, derived by conceptual translation of the long open reading frame commencing at nucleotide position 172 and ending at nucleotide position 1179 of the Hind III/Sma I restriction enzyme fragment (FIG. 4) (SEQ ID NO:4).

FIGS. 6A and 6B: Alignment of the nucleotide sequences encompassing the protein open reading frames of the *X. nematophilus* strain A24toxb4 gene (SEQ ID NO:1) and the *P. luminescens* strain V16/1 PlV16tox1 gene (SEQ ID NO:2) using the Gap program of the GCG computer software package. The *X. nematophilus* sequence is the upper line and the *P. luminescens* sequence is the lower line.

FIG. 7: Alignment of the deduced protein sequences of the extended open reading frames encoding the *X. nematophilus* A24 toxb4 protein (SEQ ID NO:3) and the *P. luminescens* strain V16/1 PlV16tox1 protein (SEQ ID NO:4) using the Gap program of the GCG computer software package. The *X. nematophilus* sequence is the upper line and the *P. luminescens* sequence is the lower line.

Figure 8:
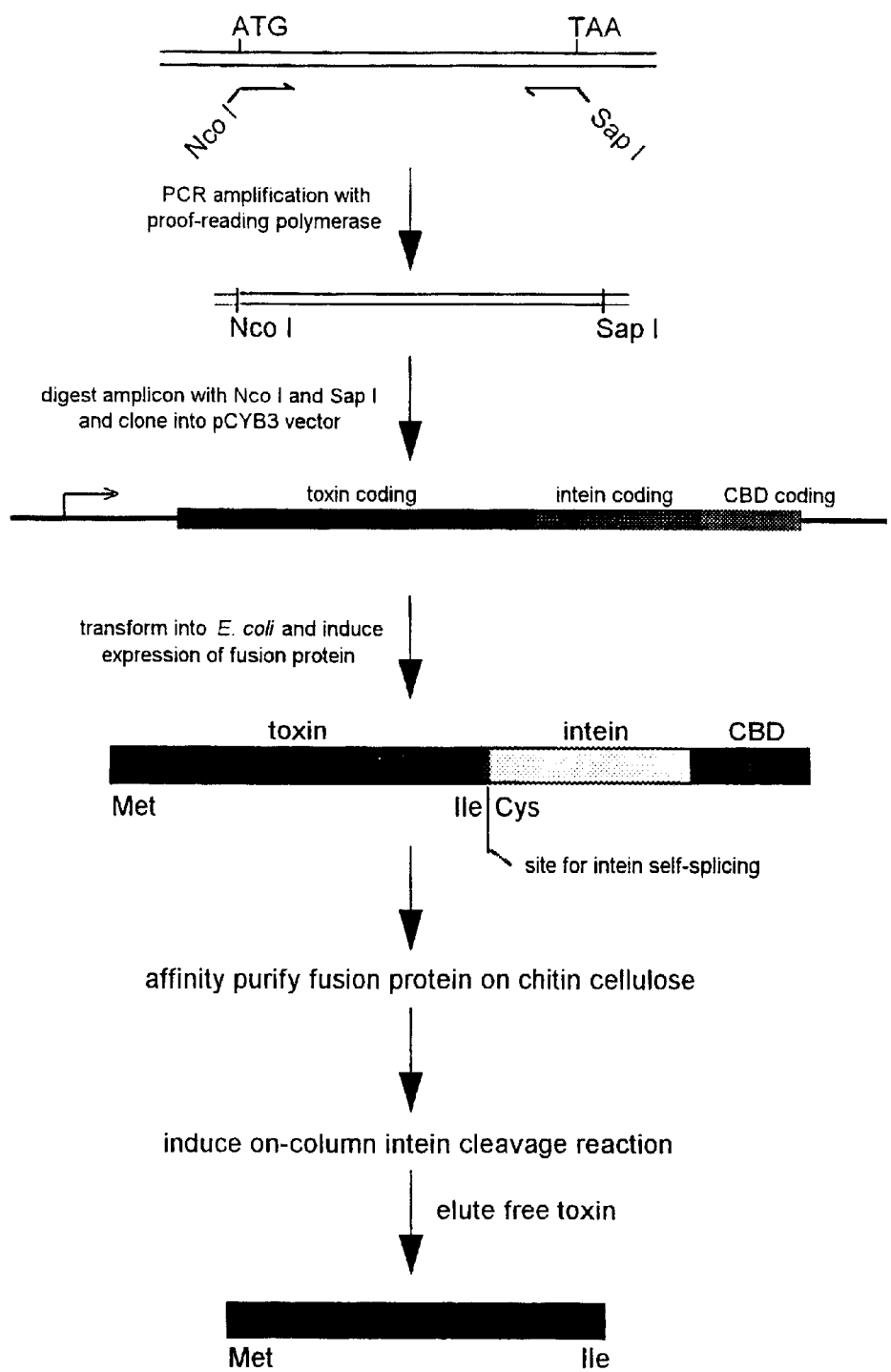

FIG. 8: Provides a scheme for expressing and isolating *X. nematophilus* A24toxb4 protein and *P. luminescens* V16/7 PlV16tox1 protein using the IMPACT™ system. The toxin protein is represented schematically as a solid black bar with the first (Met) and last (Ile) amino acids indicated.

EXAMPLE 1

Isolation and Characterisation of Toxin Genes from *Xenorhabdus nematophilus* A24 and *Photorhabdus Luminescens*

Construction of Recombinant Bacterial DNA Libraries

High molecular weight genomic DNA was isolated from *Xenorhabdus ematophilus* strain A24 using the method of Marmur (1961) and from *Photorhabdus luminescens* strain V16/1 by the method of Scott et al. (1981). The genomic DNA was partially digested with the restriction enzyme Sau 3AI to generate fragments of DNA in the size range 30 to 50 kilobase pairs and dephosphorylated by incubation with the enzyme calf intestinal alkaline phosphatase. The cosmid cloning vector “Supercos” (Stratagene) was linearised by digestion with the restriction enzyme Bam HI and ligated to the partially digested bacterial DNA at a vector:genomic DNA ratio of 1:3 according to standard procedures (Maniatis et al., 1982). The ligated DNA was packaged in vitro using Gigapack II XL Packaging Extract according to manufacturer’s instructions (Stratagene). The packaged DNA was transfected into the *Escherichia coli* strain NM554 ($F^-$, recA, araD139, Δ(ara, leu) 7696, Δlac Y74, galU–, galK–, hsr, hsm+, strA, mcrA[–], mcrA[–]). Transfected bacteria were plated onto Luria Bertani (LB) agar medium containing 150 $\mu g\ ml^{-1}$ ampicillin, to select for bacteria containing recombinant cosmid clones.

Isolation of an Insect Toxin Gene from *Xenorhabdus Nematophilus* Strain A24 by Functional Screening Cultures of bacteria harbouring individual cosmid clones were grown overnight at 28° C. in LB broth containing 150 $\mu g\ ml^{-1}$ ampicillin. The bacterial cultures were treated for 15 minutes with 2 mg $ml^{-1}$ lysozyme to create cell-free lysates. Five microliter aliquots of these lysates were injected into the haemocoel of three *Galleria mellonella* fourth instar larvae. Two clones with insecticidal activity were identified. Control lysates prepared by lysozyme treatment of *E. coli* NM554 cells containing non-recombinant Supercos vector possessed no toxin activity in the Galleria bioassay.

Characterisation of Toxin Producing Clones

Cosmid DNA from toxin-expressing clones was isolated using a standard alkaline lysis procedure (Maniatis et al., 1982). Isolated DNA was analysed by restriction enzyme digestion and agarose gel electrophoresis (Maniatis et al., 1982). Both cosmid clones appeared to contain the same region of approximately 34.6 kb of *X. nematophilus* genomic DNA. One clone, designated cos149 was chosen for further analysis.

A 7.4 kb Bam HI fragment from cos149 was ligated into the plasmid vector pGEM7Z(f)+ (Promega Biotec) and transformed into the *E. coli* strain DH5a ($F^-$, F8odlac ZΔ M15, recA1, endA1, gyrA96, thi-1, hsdR17[$r_{K-}$ $m_{K+}$] supE44, reLA1, deoR, Δ[lacZYA-argF] U169) using electroporation at 25 mF, 200 and 2.5 kV in a 0.2 cm cuvette in a Bio-Rad Gene Pulser. The resultant sub-clone was designated N8pGEM. Lysates prepared from *E. coli* cells containing the N8p GEM clone contained toxin as determined by the Galleria haemolymph injection bioassay.

A set of unidirectional deletion clones was prepared from N8pGEM according to the method of Henikoff (1984) using the Erase-a-base kit (Promega Biotec) and digestion with the enzymes Cla I and Sph I. Deleted DNA was recircularised by ligation with T4 DNA ligase and transformed into *E. coli* strain DH5α by electroporation as described above. Deletion sub-clones of varying sizes were identified and tested for toxin production using the Galleria bioassay. The smallest clone that retained toxin expression (designated tox 1) contained 1.5 kb of *X. nematophilus* DNA.

Plasmid DNA from the tox 1 clone was isolated, digested with the restriction enzymes Sac I and Hind III and directionally deleted with the Erase-a-base kit. A set of deleted clones was identified and tested for toxin production. The smallest clone retaining toxin activity (designated toxb4) contained 1.2 kb of *X. nematophilus* DNA. The toxb4 clone was sequenced on both strands with a combination of vector and gene-specific sequencing primers and ABI Prism™ di-deoxy dye-terminator sequencing mix (Applied Biosystems). Plasmid DNA was prepared by a standard alkaline lysis procedure (Maniatis et al., 1982), the double-stranded DNA was sequenced by a thermal cycle sequencing protocol, and sequencing reactions were analysed on an automated DNA sequencer (Applied Biosystems Model 377) according to manufacturer's instructions.

The toxb4 clone contained an insert 1205 bp in length (FIG. 1) which encoded a protein open reading frame of 368 amino acid residues (FIG. 2). Searches of the non-redundant Genbank nucleotide and protein databases were done for the toxb4 nucleotide and deduced protein sequences using the blastn, fasta and blastp, programs for DNA and protein sequences. No statistically significant similarity was detected between the *X. nematophilus* sequences and sequences present in the databases.

Isolation of a toxb4 Homologue from *Photorhabdus Luminescens* Strain V16/1

The genomic DNA cosmid library prepared from *P. luminescens* strain V16/1 was screened by nucleic acid hybridisation using the toxb4 gene as a hybridisation probe. Two hundred clones were grown overnight at 37° C. on LB agar plates containing 150 $\mu$g ml$^{-1}$ ampicillin and the resultant bacterial clones were transferred to nylon membrane discs (Colony/Plaque Screen™, NEN DuPont) according to the manufacturer's protocol. Colonies were lysed in situ on the membranes by treatment with 0.5 N NaOH and neutralised with 1.0M Tris-Cl, pH 7.5, and the cosmid DNA was immobilised on the membranes by air drying. Filters were pre-hybridised in a solution consisting of 5×SSPE, 0.2% w/v skim-milk powder, 0.5% w/v SDS and 0.2% mg/ml denatured salmon sperm DNA at 68° C. for 3 hours. A hybridisation probe was prepared by radiolabelling approximately 100 ng of isolated toxb4 DNA with 50 $\mu$Ci α-$^{32}$P-dATP by random-primed synthesis using the Gigaprime DNA labelling kit (GPK-1, Bresatec). Filters were incubated with the toxb4 probe in 5×SSPE, 0.2% w/v skim-milk powder, 0.5% w/v SDS and 0.2% mg/ml denatured salmon sperm DNA at 68° C. overnight. Filters were rinsed briefly in 2×SSC, and washed once for 15 min at room temperature in 2×SSC, 0.1% w/v SDS, once at 68° C. for 30 min in 0.5×SSC, 0.2% SDS. After a final rinse in 0.5×SSC filters were autoradiographed for 24 hours at –80° C. Three clones that hybridised with the toxb4 probe were identified. Cultures were grown for each clone and cell lysates were assayed for toxicity using the Galleria bioassay. Two clones, designated cos154 and cos160 showed toxin expression. Cosmid DNA was isolated from cos154 and cos160 and analysed by restriction enzyme digestion and Southern blot hybridisation. An 8.5 kb Not I restriction enzyme fragment that hybridised to the toxb4 probe was isolated from clone cos160 and sub-cloned into the Not I site of the plasmid vector pBC (KS)+ (Stratagene). Further restriction enzyme mapping and bioassay resulted in identification of a 2.4 kb Eco RI fragment that contained all the sequences necessary for production of active toxin.

Characterisation of the *P. Luminescens* Strain V16/1 Toxin Gene

Three additional sub-clones of the 2.4 kb Eco RI fragment were constructed and tested for toxin production (FIG. 3). A 1.65 kb Hind III/Eco RI fragment, a 1.39 kb Hind III/Sma I fragment and a 1.44 kb Eco RV/Eco RI fragment were each ligated into the plasmid vector pBluescript II (KS)+ (Stratagene) and the ligated DNA was transformed into *E. coli* strain DH10B™ (Stratagene) (F– mcrA Δ(mrr-hsdRMS-mcrBC) F8odlacZΔM15 ΔlacX74 deoR recA1 araD139 Δ(ara, leu)7697 galU galKl⁻ rpsL nupG). Cell lysates were prepared from cultures containing each of these sub-clones and bioassayed by haemocoel injection into Galleria larvae. Cultures containing the 1.65 kb Hind III/Eco RI fragment and the 1.39 kb Hind III/Sma I fragment expressed active toxin but cultures containing the 1.44 kb Eco RV/Eco RI fragment were inactive in the bioassay (FIG. 3). Thus, sequences located 5' to the Eco RV site of the *P. luminescens* V16/1 Hind III/Eco RI fragment are required for toxin expression from the plasmid pBluescript II (KS)+, whereas sequences 3' to the Sma I site are dispensable. The toxin gene is designated PlV16tox1 and the toxin protein encoded by this gene is designated PlV16tox1. A strategy was developed for sequencing the 1.39 kb Hind III/Sma I *P. luminescens* DNA fragment based on internal restriction enzyme sites and custom-synthesised oligonucleotide sequencing primers. The complete sequence of the 1.39 kb Hind III/Sma I fragment was determined on both strands (FIG. 4). Analysis of this DNA sequence identified a single long open reading frame 335 amino acid residues in length (FIG. 5).

Comparison of the Toxin Gene and Protein Sequences from *X. Nematophilus* and *P. Luminescens*

The DNA sequences corresponding to the deduced toxin protein open reading frames were compared for the two bacterial species using the 'Gap' program of the GCG software package. The two gene sequences are 83% identical in the coding region (FIG. 6) but show no significant similarity in the sequences immediately 5' and 3' of the extended open reading frame. The toxin protein sequences were likewise compared with the 'Gap' program and found to be 75% identical to each other and 86% similar if physico-chemically conservative amino acid differences were taken into consideration (FIG. 7). The existence of two extended insertion/deletion variants between the two proteins identifies amino acids that are not essential for toxic activity against *Galleria melonella*.

EXAMPLE 2

Distribution of the Toxin Gene from *X. Nematophilus* A24

Genomic DNA was prepared from the type strain for each of four identified Xenorhabdus species, an additional unclassified Xenorhabdus species and six *Photorhabdus luminescens* strains selected to include at least one member of each of the major genetic groups identified by analysis of 16S ribosomal RNA genes (Brunel et al., 1997). The DNA was digested with restriction enzymes, fractionated by agarose gel electrophoresis and transferred to nylon membranes by the Southern blot method (Maniatis et al., 1982). The filters were hybridised with a probe prepared from the *X. nematophilus* A24 toxb4 gene. Hybridisation conditions were selected that would allow sequences with an average identity of approximately 65% to be detected. The results are shown in Table 1.

TABLE 1

| Bacterial species | Strain | Toxin gene† |
|---|---|---|
| *Xenorhabdus nematophilus* | A24 | + |
| *Xenorhabdus nematophilus* | AN6 | + |
| *Xenorhabdus poinarii* | G6 | − |
| *Xenorhabdus beddingii* | Q58 | − |
| *Xenorhabdus bovienii* | T28 | − |
| Xenorhabdus sp. | K77 | − |
| *Photorhabdus luminescens* | Hb | − |
| *Photorhabdus luminescens* | Hm | − |
| *Photorhabdus luminescens* | C1 | − |
| *Photorhabdus luminescens* | V16 | + |
| *Photorhabdus luminescens* | C8406 | + |
| *Photorhabdus luminescens* | K81 | + |

†+ indicates presence of hybridising DNA, − indicates absence of hybridisation of toxin gene probe.

Clearly, homologues of the toxin gene from *X. nematophilus* A24 is present in some species of the genus Xenorhabdus, and some, but not all isolates of *Photorhabdus luminescens*.

EXAMPLE 3

Activity of Toxin Genes Cloned into Plasmid Vectors and Transformed into *E. Coli*

Active toxin protein was expressed when the A24 toxb4 clone or V16 tox1 genes were inserted into general plasmid vectors of the type pGEM (Promega Biotec) or pBluescript (Stratagene) and the recombinant plasmids transformed into *E. coli*. More specifically, the *X. nematophilus* toxin A24 toxb4gene was cloned into the plasmid pGEM7z and the *P. luminescens* V16 tox1 gene was cloned into pBluescript SK.
Preparation of Cell Extract A culture of *E. coli* cells transformed with either a recombinant plasmid containing a toxin gene or a non-recombinant parent plasmid was grown overnight at 37° C. in nutrient broth. Lysozyme was added to the culture to a final concentration of 1 mg/ml and the mixture left at room temperature for 30 minutes to lyse the cells. The cleared lysate was used directly for bioassay.
Bioassay Extracts were bioassayed using the intrahaemocoel injection assay. Ten microliters of *E. coli* cell lysate were injected into the abdominal region of a *Galleria mellonella* larvae through an intersegmental membrane. Bioassays were done on 10 larvae for each extract and injected larvae were held at 22° C. Mortality was recorded daily. Results are shown in Table 2.

TABLE 2

| | Percentage mortality | | | | |
|---|---|---|---|---|---|
| Toxin source | Day 1 | Day 2 | Day 3 | Day 4 | Day 5 |
| PlV16tox1 | 0 | 20 | 40 | 90 | 100 |
| pBluescript SK (control) | 0 | 10 | 10 | 10 | 20 |
| A24toxb4 | 10 | 10 | 10 | 100 | 100 |
| PGEM7z (control) | 0 | 0 | 10 | 20 | 20 |

Extracts prepared from *E. coli* cells transformed with recombinant plasmids containing the toxin gene from either *X. nematophilus* A24 or *P. luminescens* strain V16/1 kill *G. mellonella* larvae and caused complete mortality of injected individuals five days after injection. Extracts prepared from cells containing only the plasmid vectors pBluescript SK or pGEM7z did not kill the larvae.

Effect of Temperature on Toxicity

Extracts were prepared from *E. coli* cells transformed either with cloned toxin genes or the empty plasmid vector controls and injected into *G. mellonella* larvae as described previously. The injected larvae were maintained at either 20° C. or 25° C. Results are shown in Table 3.

TABLE 3

| | | Percentage mortality | | | | | |
|---|---|---|---|---|---|---|---|
| Toxin source | Temp | Day 1 | Day 2 | Day 3 | Day 4 | Day 5 | Day 6 |
| PlV16tox1 | 20° C. | 0 | 10 | 25 | 60 | 90 | 100 |
| PlV16tox1 | 25° C. | 0 | 0 | 100 | 100 | 100 | 100 |
| pBluescript SK | 20° C. | 0 | 0 | 0 | 0 | 0 | 0 |
| pBluescript SK | 25° C. | 0 | 5 | 10 | 10 | 15 | 15 |
| A24toxb4 | 20° C. | 5 | 30 | 35 | 65 | 95 | 100 |
| A24toxb4 | 25° C. | 60 | 75 | 100 | 100 | 100 | 100 |
| pGEM7z | 20° C. | 0 | 5 | 5 | 5 | 5 | 5 |
| pGEM7z | 25° C. | 0 | 5 | 5 | 5 | 5 | 5 |

Extracts prepared from cells containing either the cloned toxin gene from *X. nematophilus* A24 or the *P. luminescens* V16 toxin gene killed all larvae within three days for larvae held at 25° C. or by six days for larvae maintained at 20° C. following injection. Control extracts prepared from cells containing only the cloning vectors pBluescript or pGEM7z did not cause significant larval mortality.

EXAMPLE 4

Toxin Activity Against Different Insect Species (1) *Helicoverpa Armigera* (Lepidoptera:Noctuidae) Bioassay Extracts were bioassayed using the intrahaemocoel injection assay. Ten microliters of *E. coli* cell lysate were injected into the abdominal region of fourth instar *Helicoverpa armigera* larvae through an intersegmental membrane. Bioassays were done on 24 larvae for each extract and injected animals were held at 27° C. Mortality was recorded daily. Results are shown in Table 4.

TABLE 4

| | Percentage mortality | | | |
|---|---|---|---|---|
| Toxin source | Day 1 | Day 2 | Day 3 | Day 4 |
| PlV16tox1 | 38 | 71 | 87 | 91 |
| pBluescript SK | 4 | 4 | 8 | 8 |
| A24toxb4 | 50 | 87 | 91 | 91 |
| pGEM7z | 0 | 0 | 0 | 0 |

Extracts prepared from *E. coli* cells transformed with recombinant plasmids containing the toxin gene from either *X. nematophilus* A24 or *P luminescens* strain V16/1 caused significant mortality to injected larvae within 24 hours after injection. All larvae died by 4 days following the injection, with the exception of a small number of "escapees" that resulted from leakage of injected material upon removal of the injection needle. Extracts prepared from cells containing only the plasmid vectors pBluescript SK or pGEM7z had no significant effect on *H. armigera* larvae.

(2) *Plodia interpunctella* (Lepidoptera:) Bioassay

Extracts were bioassayed using the intrahaemocoel injection assay. Five microliters of *E. coli* cell lysate were injected into the abdominal region of a final instar *Plodia interpunctella* larva through an intersegmental membrane. Bioassays were done on 20 wandering-stage larvae for each extract and injected animals were held at 26° C. Mortality was recorded daily. Results are shown in Table 5.

TABLE 5

| Toxin source | Percentage mortality | | |
|---|---|---|---|
| | Day 1 | Day 2 | Day 3 |
| PlV16tox1 | 20 | 90 | 100 |
| pBluescript SK | 0 | 0 | 0 |
| A24toxb4 | 75 | 95 | 100 |
| pGEM7z | 0 | 5 | 5 |

Extracts prepared from *E. coli* cells transformed with recombinant plasmids containing the toxin gene from either *X. nematophilus* A24 or *P. luminescens* strain V16/1 caused significant mortality to injected larvae within 24 hours after injection. All larvae had died within 3 days. Extracts prepared from cells containing only the plasmid vectors pBluescript SK or pGEM7z had no significant effect on survival of *P. interpunctella* larvae.

(3) *Lucilia cuprina* (Dip tera: Calliphoridae) Adults Bioassay

Extracts were bioassayed using the intrahaemocoel injection assay. Five microliters of *E. coli* cell lysate were injected into the abdomen of a 3 day old *Lucilia cuprina* female fly through an intersegmental membrane. Bioassays were done on 20 flies for each extract and injected animals were held at 25° C. Mortality was recorded daily. Results are shown in Table 6.

TABLE 6

| Toxin source | Percentage mortality | | | |
|---|---|---|---|---|
| | Day 1 | Day 2 | Day 3 | Day 4 |
| PlV16tox1 | 55 | 65 | 85 | 100 |
| pBluescript SK | 20 | 25 | 25 | 25 |
| A24toxb4 | 55 | 75 | 85 | 100 |
| pGEM7z | 30 | 60 | 65 | 65 |

Extracts prepared from *E. coli* cells transformed with recombinant plasmids containing the toxin gene from either *X. nematophilus* A24 or *P luminescens* strain V16/1 caused significant mortality to injected flies within 24 hours of injection. All flies died by 4 days after injection. Extracts prepared from cells containing only the plasmid vectors pBluescript SK or pGEM7z also caused significant mortality to the *L. cuprina* flies in the first 48 hours following injection. After this control mortality stabilised, there was no further deaths for the remainder of the test period. Additional experiments with saline injections showed that the early mortality in the control group resulted from physical damage to the flies as a result of the injection process.

(4) *Lucilia cuprina* (Diptera:Calliphoridae) Larvae Bioassay

Extracts were bioassayed using the intrahaemocoel injection assay. Five microliters of *E. coli* cell lysate were injected into the abdominal cavity of wandering-stage final instar Lucilia cuprina larvae through an intersegmental membrane. Bioassays were done on 20 larvae for each extract and injected animals were held at 25° C. Mortality was recorded daily. Results are shown in Table 7.

TABLE 7

| Toxin source | Percentage mortality | | | |
|---|---|---|---|---|
| | Day 1 | Day 2 | Day 3 | Day 4 |
| PlV16tox1 | 35 | 45 | 75 | 80 |
| pBluescript SK | 25 | 30 | 30 | 30 |
| A24toxb4 | 10 | 35 | 90 | 95 |
| pGEM7z | 15 | 20 | 20 | 25 |

Extracts prepared from *E. coli* cells transformed with recombinant plasmids containing the toxin gene from either *X. nematophilus* A24 or *P. luminescens* strain V16/1 caused significant mortality to injected larvae within 48 hours of injection. All larvae died by 4 days after injection, with the exception of a small number of "escapees" resulting from leakage at the time of needle withdrawal as previously described for *H. armigera*. As with the *L. cuprina* adults, extracts prepared from cells containing only the plasmid vectors pBluescript SK or pGEM7z caused significant mortality to the *L. cuprina* larvae in the first 48 hours following injection. After this, control mortality stabilised and there were no further deaths in this group of larvae for the remainder of the test period. As described above, experiments with saline injections showed that this early mortality in the control group resulted from physical damage to the larvae as a result of the injection process.

(5) *Aphis Gossypii* (Hemiptera:Aphididae) Nymphs Bioassay

Extracts were prepared from *E. coli* cells containing either the *X. nematophilus* toxin gene or the empty plasmid vector pGEM7z. The extracts were incorporated into a defined liquid diet at a concentration of 10% by volume and aphids were provided ad libitum access to diet for a period of five days. Results are shown in Table 8.

TABLE 8

| Treatment | % Mortality at day 5 | Average Number of Moults |
|---|---|---|
| Control† | 10 | 1.9 |
| pGEM7z extract | 0 | 2 |
| A24toxb4 extract | 90 | 0.6 |

†an additional treatment consisting of diet supplemented with lysozyme at the same final concentration used to prepare the *E. coli* cell extracts was included as a control for any potential effects of the lysozyme.

The *X. nematophilus* A24 toxin effectively blocked growth as seen from the reduction in the number of nymphal moults, and by five days had killed most of the larvae. Thus, the *X. nematophilus* A24 toxin was orally insecticidal to *Aphis gossypii*.

EXAMPLE 5

Expression and Purification of the Full-length Toxin Protein from *X. Nematophilus*

Further characterisation of the properties of the toxins encoded by the cloned genes from *X. nematophilus* A24 and *P. luminescens* V16/1 required expression of the full-length protein in a format that allowed for affinity purification of the toxin. This was achieved by expressing the full-length toxin as a fusion protein in which the fusion partner was used for affinity selection, and the toxin domain was cleaved off chemically after the purification stage. A suitable expression and purification system is the IMPACT™ system (New England Biolabs) in which the toxin open reading frame is cloned at the 5' end of a self-splicing intein coding sequence fused to a short DNA sequence encoding a chitin binding domain.

Recombinant plasmids containing both the *X. nematophilus* A24 toxin and the *P. luminescens* V16/1 toxin genes were prepared in the IMPACT™ vector pCYB3 (FIG. 8). Preparation of these constructs required the engineering of a unique restriction enzyme site at each end of the toxin open reading frame that enabled in-frame insertion of the toxin gene into the expression vector such that translation began at the Methionine initiation codon of the toxin protein and a cleavage site for protein splicing was placed immediately adjacent to the final residue of the toxin open reading frame. Expression of the fusion proteins in *E. coli*, preparation of bacterial cell extracts, affinity isolation of the fusion proteins on chitin cellulose columns, on-column DTT-mediated cleavage of the fusion proteins and elution of the purified toxin proteins were all performed according to the manufacturer's instructions (IMPACT™ system manual, New England Biolabs)

For both toxin constructs a major protein product of the expected size (approximately 40 kDa) was detected by SDS polyacrylamide gel electrophoretic analysis of the column eluate. The preparations contained several other proteins but these comprised less than 10% of the total protein present in the samples as determined by Coomassie blue staining of the polyacrylamide gels. Approximately 750 μg of PlV16tox1 toxin and 1.5 mg of A24toxb4 toxin were isolated from one liter of *E. coli* broth cultures. Purified proteins were dialysed against phosphate-buffered saline and simultaneously concentrated by diafiltration to a final concentration of approximately 1 mg/ml on Millipore spin cartridges with a membrane nominal molecular weight cut-off of 10 kDa according to manufacturer's instructions (Millipore).

EXAMPLE 6

Biological Activity of Purified Toxin Proteins

Bioassay

The activity of the purified *X. nematophilus* and *P. luminescens* toxins were determined by intra-haemocoel injection bioassay on *Galleria mellonella* and *Helicoverpa armigera* larvae as described above. The toxin protein preparations were diluted in phosphate-buffered saline and 10 ml of protein solution was injected into each larva. Ten larvae were injected for each protein concentration and mortality was recorded at 12 hour intervals for six days after injection. Proteins were tested over a dose range from 1 nanogram ($10^{-9}$ g) to 1 microgram ($10^{-6}$ g) of protein per larva. An inert protein, *E. coli* maltose binding protein, was prepared in the IMPACT™ system, purified and concentrated according to the same methods used for the two toxin proteins. The purified maltose binding protein was used as a control for these experiments. The maltose binding protein did not cause larval mortality at any of the quantities tested. The results are shown in Tables 9 to 12.

TABLE 9

Effect of purified PlV16 tox1 toxin on *G. mellonella* larvae

Percentage Mortality

| Protein Injected | Day 2 am | Day 2 pm | Day 3 am | Day 3 pm | Day 4 am | Day 4 pm | Day 5 am | Day 5 pm | Day 6 am |
|---|---|---|---|---|---|---|---|---|---|
| 1 ng | 0 | 0 | 0 | 0 | 0 | 0 | 0 | 0 | 0 |
| 10 ng | 0 | 0 | 0 | 0 | 0 | 0 | 0 | 0 | 10 |
| 20 ng | 0 | 10 | 10 | 20 | 20 | 20 | 20 | 30 | 30 |
| 100 ng | 0 | 0 | 30 | 40 | 60 | 70 | 80 | 80 | 100 |
| 200 ng | 0 | 0 | 44 | 56 | 56 | 78 | 100 | 100 | 100 |
| 1000 ng | 20 | 20 | 60 | 60 | 100 | 100 | 100 | 100 | 100 |

TABLE 10

Effect of purified A24 toxb4 toxin on *G. mellonella* larvae

Percentage Mortality

| Protein Injected | Day 2 am | Day 2 pm | Day 3 am | Day 3 pm | Day 4 am | Day 4 pm | Day 5 am | Day 5 pm | Day 6 am |
|---|---|---|---|---|---|---|---|---|---|
| 1 ng | 0 | 0 | 0 | 0 | 0 | 0 | 0 | 0 | 0 |
| 10 ng | 0 | 0 | 0 | 0 | 0 | 0 | 0 | 0 | 0 |
| 20 ng | 0 | 0 | 10 | 20 | 20 | 40 | 60 | 70 | 80 |
| 100 ng | 10 | 10 | 20 | 30 | 30 | 50 | 90 | 100 | 100 |
| 200 ng | 0 | 0 | 0 | 0 | 50 | 70 | 70 | 90 | 100 |
| 1000 ng | 0 | 0 | 0 | 10 | 60 | 80 | 100 | 100 | 100 |

TABLE 11

Effect of purified PlV16 tox1 toxin on *H. armigera* larvae

Percentage Mortality

| Protein Injected | Day 1/ am | Day 1/ pm | Day 2/ am | Day 2/ pm | Day 3/ am | Day 3/ pm | Day 4/ am | Day 4/ pm |
|---|---|---|---|---|---|---|---|---|
| 1 ng | 0 | 0 | 0 | 0 | 0 | 0 | 0 | 0 |
| 10 ng | 0 | 0 | 0 | 0 | 0 | 0 | 0 | 0 |
| 20 ng | 0 | 10 | 10 | 10 | 10 | 10 | 10 | 10 |
| 100 ng | 30 | 30 | 50 | 50 | 60 | 70 | 70 | 70 |
| 200 ng | 0 | 0 | 80 | 80 | 80 | 80 | 80 | 80 |
| 1000 ng | 22 | 67 | 100 | 100 | 100 | 100 | 100 | 100 |

TABLE 12

Effect of purified A24 toxb4 toxin on *H. armigera* larvae

Percentage Mortality

| Protein Injected | Day 1/ am | Day 1/ pm | Day 2/ am | Day 2/ pm | Day 3/ am | Day 3/ pm | Day 4/ am | Day 4/ pm |
|---|---|---|---|---|---|---|---|---|
| 1 ng | 0 | 0 | 0 | 0 | 0 | 0 | 0 | 0 |
| 10 ng | 0 | 30 | 50 | 70 | 90 | 90 | 90 | 90 |
| 20 ng | 0 | 30 | 50 | 80 | 90 | 90 | 90 | 90 |
| 100 ng | 0 | 20 | 80 | 100 | 100 | 100 | 100 | 100 |
| 200 ng | 0 | 30 | 90 | 100 | 100 | 100 | 100 | 100 |
| 1000 ng | 20 | 60 | 100 | 100 | 100 | 100 | 100 | 100 |

Both the *X. nematophilus* A24 toxin and the *P. luminescens* V16/1 toxin killed a high percentage of larvae after a single injection of at least 20 ng of toxin protein per larva. Mortality was dependent on toxin type and concentration.

*H. armigera* was sensitive to small quantities of *X. nematophilus* A24 toxin with high mortality at 10–20 ng of toxin per larva, but was less sensitive to *P. luminescens* V16/1 toxin where significant mortality was observed only for quantities greater than 20 ng of protein per larva. A similar pattern of sensitivity was observed for *G. mellonella* larvae. The time taken to kill the larvae of either species was not strongly dependent on the time since toxin injection, although larger amounts of toxin killed more quickly. However, at all quantities greater than, or equal to 20 ng per larva the insects were effectively dead, because the *H. armigera* larvae ceased feeding and *G. mellonella* larvae were unable to spin cocoon silk.

Thus, the proteins encoded by the A24 toxb4 genes of *X. nematophilus* and the PlV16 tox1 gene of *P. luminescens* encode toxin proteins that are effective insecticides, especially of lepidopterous larvae including *G. mellonella*, *H. armigera* and *P. interpunctella*, when delivered into insect haemocoel.

EXAMPLE 7

Effect of Purified Toxin on Insect Cells in Culture

The purified *X nematophilus* A24 toxin and *P. luminescens* V16/1 toxin and the maltose binding protein control were each tested for their effects on the growth and viability of insect cells in tissue culture. A sample of $10^4$ cells in the appropriate culture medium was mixed with the test proteins at several different concentrations and seeded into the wells of A 96-well tissue culture plate. Cells were allowed to grow for 24 hours at 25° C. and cells were counted in a haemocytometer and assessed visually for cell lysis. The results are shown in Table 13.

For all cell lines, at all protein concentrations tested the maltose binding protein control had no effect on cell growth or viability. Neither of the toxin proteins had any significant effect on cell growth or viability for the *Drosophila melanogaster* Schneider 2 cell line. The *X. nematophilus* A24 toxin caused significant cell growth inhibition and cytotoxicity to the lepidopteran High-Five cell line at concentrations above 0.1 g/ml. The *P. luminescens* V16 toxin caused slight growth inhibition only at the highest concentration tested of 1 µg/ml. The *X. nematophilus* A24 toxin caused significant cell growth inhibition and cytotoxicity to the lepidopteran Sf9 cell line at concentrations above 0.001 µg/ml, and the *P. luminescens* V16 toxin was toxic to this cell line at concentrations of 0.1 µg/ml and higher. Thus, toxins of this family exhibit growth inhibitory and cytotoxic activity against insect cells in tissue culture, especially cell lines of lepidopteran origin. Similar tests with a mouse hybridoma cell line demonstrated slight growth inhibition only by the *X. nematophilus* A24 toxin, and only at the highest concentration tested of 1 µg/ml.

TABLE 13

| Cell Line | Treatment | | |
|---|---|---|---|
| | Toxin | Concentration µg/ml | Cells/well |
| Schneider 2 | PlV16tox1 | 0 | $4.1 \times 10^4$ |
| " | " | 0.001 | ND† |
| " | " | 0.1 | $4.1 \times 10^4$ |
| " | " | 1 | $4.6 \times 10^4$ |
| Schneider 2 | A24toxb4 | 0 | $3.7 \times 10^4$ |
| " | " | 0.001 | ND |
| " | " | 0.1 | $3.6 \times 10^4$ |
| " | " | 1 | $3.4 \times 10^4$ |
| High-Fives | PlV16tox1 | 0 | $3.8 \times 10^4$ |
| " | " | 0.001 | ND |
| " | " | 0.1 | $3.9 \times 10^4$ |
| " | " | 1 | $2.9 \times 10^4$ |
| High-Fives | A24toxb4 | 0 | $8.2 \times 10^4$ |
| " | " | 0.001 | $7.1 \times 10^4$ |
| " | " | 0.1 | $2.5 \times 10^4$ |
| " | " | 1 | $2.5 \times 10^4$ |
| Sf9 | PlV16tox1 | 0 | $3.6 \times 10^4$ |
| " | " | 0.001 | $4.3 \times 10^4$ |
| " | " | 0.1 | $7 \times 10^3$ |
| " | " | 1 | $6 \times 10^3$ |
| Sf9 | A24toxb4 | 0 | $4.7 \times 10^4$ |
| " | " | 0.001 | $1 \times 10^4$ |
| " | " | 0.1 | $5 \times 10^3$ |
| " | " | 1 | $6.5 \times 10^3$ |

†ND: cell numbers not determined

As will be appreciated by persons skilled in this field, the present invention provides a new class of toxins useful for genetically engineering a wide range of biological systems which will thus become more useful for control of pest insects detrimental to agricultural, aquatic and forest industries. This new class of toxin may be purified by one or more methods of protein purification well known in the art. Insecticidal fragments may be generated from the purified toxin using, for example, cleavage with trypsin or cyanogen bromide.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Brunel, B., Givaudin, A., Lanois, A., Akhurst, R. J. and Boemare, N. (1997). Fast and accurate identification of Xenorhabdus and Photorhabdus species by restriction analysis of PCR-amplified 16S rRNA genes. *Applied and Envirnomental Microbiology* 63, 574–580.

Henikoff, S. (1984). Unidirectional digestion with exonuclease III creates targeted breakpoints for DNA sequencing, Gene 28, 351–359.

Innis, M. A., Gelford, D. H., Sminsky, J. J. and White, T. J. (1990). PCR Protocols: A Guide to Methods and Applications. Academic Press, San Diego.

Maniatis, T., Fritsch, E. F. and Sambrook, J. (1982). Molecular cloning: A laboratory manual. Cold spring Harbor Laboratory, Cold spring Harbor, N.Y.

Marmur J. (1961). A procedure for the isolation of deoxyribonucleic acid from micro organisms.

Scott, K. F., Rolfe, B. G. and Shine, J. (1981). Biological nitrogen fixation: primary structure of the *Klebsiella pneumoniae* nifH and nifD genes. J. Mol. Appl. Genet. 1, 71–81.

What is claimed is:

1. An isolated polynucleotide molecule encoding an insecticidal toxin, said polynucleotide molecule comprising a nucleotide sequence shown as SEQ ID NO:1.

2. A recombinant microorganism, the microorganism being characterised in that it is transformed with and expresses the polynucleotide molecule according to claim 1.

3. The recombinant microorganism according to claim 2 wherein the microorganism is selected from the group consisting of a bacterium, a protozoon and a yeast.

4. A method of producing an insecticidal toxin, said method comprising:
   (i) culturing the microorganism according to claim 2 under conditions suitable for the expression of the polynucleotide molecule; and
   (ii) recovering the insecticidal toxin.

5. A plant transformed with, and capable of expressing the polynucleotide molecule according to claim 1.

* * * * *

SEQUENCE LISTING

<160> NUMBER OF SEQ ID NOS: 20

<210> SEQ ID NO 1
<211> LENGTH: 1107
<212> TYPE: DNA
<213> ORGANISM: Xenorhabdus nematophilus

<400> SEQUENCE: 1

| | | | | | |
|---|---|---|---|---|---|
| atggttatta | aacccgtaac | aactccgagt | gtaatacaat | taacgcctga | tgatagagta | 60 |
| acgcctgatg | ataaaggtga | atatcaaccc | gttgaaaagc | aaatagcggg | agatataata | 120 |
| cgtgtactag | aattcaagca | aacaaatgaa | agtcatacag | gattgtatgg | aattgcatat | 180 |
| cgagctaaga | agtaataat | agcatatgct | ttagcggtaa | gtggtattca | taatgtctct | 240 |
| caacttccag | aagactatta | taaaaataag | gataacacag | gtagaattta | tcaagaatac | 300 |
| atgtctaatc | ttttatctgc | actattgggt | gagaatggtg | atcaaatttc | taagatatg | 360 |
| gcaaatgatt | tacccagaa | cgaactggag | tttggaggtc | aacgtcttaa | aaatacctgg | 420 |
| gatattcctg | atcttgagaa | taaactattg | gaagattatt | cagatgaaga | taaattatta | 480 |
| gcactatatt | tctttgcttc | acaagaactt | ccaatggagg | caaatcaaca | atcaaatgca | 540 |
| gcaaattttt | ttaaagtaat | tgattttta | cttatcttat | ctgctgtaac | atcactggga | 600 |
| aaaaggattt | tttcaaaaaa | tttttacaat | ggtctagaaa | ctaaatcatt | agagaattat | 660 |
| attgagagaa | aaaacttc | taaacctttc | tttcgaccac | cgcagaagtt | acctgatggc | 720 |
| agaacaggct | acttggccgg | tccaacaaaa | gcgcctaaat | tgccaacaac | gtcttctaca | 780 |
| gcaacaacgt | ctacagcagc | ttcatctaat | tggagagtta | gtttgcaaaa | acttagagat | 840 |
| aacccatcca | gaaatacatt | tatgaaaatg | gatgatgctg | caaaacgaaa | atatagttca | 900 |
| tttataaaag | aggtacaaaa | gggtaatgat | ccacgtgcag | cagcagcaag | tattggtaca | 960 |
| aaaagcggca | gtaacttcga | aaaactgcaa | ggtagagatt | tatatagtat | aagactaagc | 1020 |
| caagaacaca | gggtaacatt | ctccataaat | aatactgacc | aaataatgga | gatccaaagt | 1080 |
| gttggaactc | attaccaaaa | tatataa | | | | 1107 |

<210> SEQ ID NO 2
<211> LENGTH: 1008
<212> TYPE: DNA
<213> ORGANISM: Photorhabdus luminescens

<400> SEQUENCE: 2

| | | | | | |
|---|---|---|---|---|---|
| atggttatac | aattaacacc | tgatgataga | agtggatatc | cacccgttga | aaagcaaata | 60 |
| gcaggagata | tagtacgtat | actaaacttt | aagcaaacag | atgagggtca | tacagcatca | 120 |
| tatggaattg | aatatcgagc | taagaaaata | atattagctt | acgctttggc | tgtaagtggt | 180 |
| attcataatg | tatctaaact | tcctgatgac | tattataaga | ataaagagac | tgctgagaga | 240 |
| atttatcaag | aatatatgtc | taatctttca | tctgcactat | taggtgaaaa | tggtgatcaa | 300 |
| atttctaaag | atatggcaaa | tggttttat | aagaatgaac | tggattttga | aggtcaatat | 360 |
| cctcaaaaca | tttggaatgt | tcctgagctt | gaaaataaac | cattgagtgc | ttattcagat | 420 |
| gacgataaat | tattagcact | atattttttc | tctgtacagg | aaattccact | ggaggaaaat | 480 |
| caacaatcaa | atgccgcaag | attttttaaa | ttaattgatt | tcttatttac | cttatctgct | 540 |
| gtaacttcac | tgggaaggag | gatttttca | aaaaacttt | acaatggatt | agaggctaaa | 600 |
| tcattagaga | attatattga | gagaaaaaaa | cttctaaac | cttctttcg | accaccgcag | 660 |

-continued

```
agattacctg atggcagaat aggttatttg gctggaccaa cagaagcgcc taaatggaga    720
gtgagtttta aagaacttaa aaataacaaa tctaggaatg gatttttctaa tatggaaggg   780 gctgcaaaac aaaagtatag ttcatttata aagaggtac aaaagggtaa cgctccacag    840
acagcagcga aaagtattgg tacagccagt ggcagtaacc tggaaaaatt gccgaataat   900
ttatatagtg tgaggctaag ccaaaaagac agggtaacct ttactcaaaa tgatactgac   960
aatacaatga cggttcatag tgttggaact cattataaaa atatatga              1008
```

<210> SEQ ID NO 3
<211> LENGTH: 368
<212> TYPE: PRT
<213> ORGANISM: Xenorhabdus nematophilus

<400> SEQUENCE: 3

Met Val Ile Lys Pro Val Thr Thr Pro Ser Val Ile Gln Leu Thr Pro
1               5                   10                  15

Asp Asp Arg Val Thr Pro Asp Lys Gly Glu Tyr Gln Pro Val Glu
            20                  25                  30

Lys Gln Ile Ala Gly Asp Ile Ile Arg Val Leu Glu Phe Lys Gln Thr
        35                  40                  45

Asn Glu Ser His Thr Gly Leu Tyr Gly Ile Ala Tyr Arg Ala Lys Lys
    50                  55                  60

Val Ile Ile Ala Tyr Ala Leu Ala Val Ser Gly Ile His Asn Val Ser
65                  70                  75                  80

Gln Leu Pro Glu Asp Tyr Tyr Lys Asn Lys Asp Asn Thr Gly Arg Ile
                85                  90                  95

Tyr Gln Glu Tyr Met Ser Asn Leu Leu Ser Ala Leu Leu Gly Glu Asn
            100                 105                 110

Gly Asp Gln Ile Ser Lys Asp Met Ala Asn Asp Phe Thr Gln Asn Glu
        115                 120                 125

Leu Glu Phe Gly Gly Gln Arg Leu Lys Asn Thr Trp Asp Ile Pro Asp
    130                 135                 140

Leu Glu Asn Lys Leu Leu Glu Asp Tyr Ser Asp Glu Asp Lys Leu Leu
145                 150                 155                 160

Ala Leu Tyr Phe Phe Ala Ser Gln Glu Leu Pro Met Glu Ala Asn Gln
                165                 170                 175

Gln Ser Asn Ala Ala Asn Phe Phe Lys Val Ile Asp Phe Leu Leu Ile
            180                 185                 190

Leu Ser Ala Val Thr Ser Leu Gly Lys Arg Ile Phe Ser Lys Asn Phe
        195                 200                 205

Tyr Asn Gly Leu Glu Thr Lys Ser Leu Glu Asn Tyr Ile Glu Arg Lys
    210                 215                 220

Lys Leu Ser Lys Pro Phe Phe Arg Pro Gln Lys Leu Pro Asp Gly
225                 230                 235                 240

Arg Thr Gly Tyr Leu Ala Gly Pro Thr Lys Ala Pro Lys Leu Pro Thr
                245                 250                 255

Thr Ser Ser Thr Ala Thr Thr Ser Thr Ala Ala Ser Ser Asn Trp Arg
            260                 265                 270

Val Ser Leu Gln Lys Leu Arg Asp Asn Pro Ser Arg Asn Thr Phe Met
        275                 280                 285

Lys Met Asp Asp Ala Ala Lys Arg Lys Tyr Ser Ser Phe Ile Lys Glu
    290                 295                 300

Val Gln Lys Gly Asn Asp Pro Arg Ala Ala Ala Ala Ser Ile Gly Thr

```
Lys Ser Gly Ser Asn Phe Glu Lys Leu Gln Gly Arg Asp Leu Tyr Ser
                325                 330                 335

Ile Arg Leu Ser Gln Glu His Arg Val Thr Phe Ser Ile Asn Asn Thr
                340                 345                 350

Asp Gln Ile Met Glu Ile Gln Ser Val Gly Thr His Tyr Gln Asn Ile
                355                 360                 365

<210> SEQ ID NO 4
<211> LENGTH: 335
<212> TYPE: PRT
<213> ORGANISM: Photorhabdus luminescens

<400> SEQUENCE: 4

Met Val Ile Gln Leu Thr Pro Asp Asp Arg Ser Gly Tyr Pro Pro Val
1               5                   10                  15

Glu Lys Gln Ile Ala Gly Asp Ile Val Arg Ile Leu Asn Phe Lys Gln
                20                  25                  30

Thr Asp Glu Gly His Thr Ala Ser Tyr Gly Ile Glu Tyr Arg Ala Lys
                35                  40                  45

Lys Ile Ile Leu Ala Tyr Ala Leu Ala Val Ser Gly Ile His Asn Val
            50                  55                  60

Ser Lys Leu Pro Asp Asp Tyr Tyr Lys Asn Lys Glu Thr Ala Glu Arg
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asn Gly Phe Tyr Lys Asn
                100                 105                 110

Glu Leu Asp Phe Glu Gly Gln Tyr Pro Gln Asn Ile Trp Asn Val Pro
            115                 120                 125

Glu Leu Glu Asn Lys Pro Leu Ser Ala Tyr Ser Asp Asp Lys Leu
            130                 135                 140

Leu Ala Leu Tyr Phe Phe Ser Val Gln Glu Ile Pro Leu Glu Asn
145                 150                 155                 160

Gln Gln Ser Asn Ala Ala Arg Phe Phe Lys Leu Ile Asp Phe Leu Phe
                165                 170                 175

Thr Leu Ser Ala Val Thr Ser Leu Gly Arg Arg Ile Phe Ser Lys Asn
            180                 185                 190

Phe Tyr Asn Gly Leu Glu Ala Lys Ser Leu Glu Asn Tyr Ile Glu Arg
            195                 200                 205

Lys Lys Leu Ser Lys Pro Phe Phe Arg Pro Pro Gln Arg Leu Pro Asp
210                 215                 220

Gly Arg Ile Gly Tyr Leu Ala Gly Pro Thr Glu Ala Pro Lys Trp Arg
225                 230                 235                 240

Val Ser Phe Lys Glu Leu Lys Asn Asn Lys Ser Arg Asn Gly Phe Ser
                245                 250                 255

Asn Met Glu Gly Ala Ala Lys Gln Lys Tyr Ser Ser Phe Ile Lys Glu
            260                 265                 270

Val Gln Lys Gly Asn Ala Pro Gln Thr Ala Ala Lys Ser Ile Gly Thr
            275                 280                 285

Ala Ser Gly Ser Asn Leu Glu Lys Leu Pro Asn Asn Leu Tyr Ser Val
            290                 295                 300

Arg Leu Ser Gln Lys Asp Arg Val Thr Phe Thr Gln Asn Asp Thr Asp
305                 310                 315                 320
```

Asn Thr Met Thr Val His Ser Val Gly Thr His Tyr Lys Asn Ile
                325                 330                 335

<210> SEQ ID NO 5
<211> LENGTH: 1205
<212> TYPE: DNA
<213> ORGANISM: Xenorhabdus nematophilus

<400> SEQUENCE: 5

| | | | | | |
|---|---|---|---|---|---|
| ataatgggaa | agtacaatgg | ttattaaacc | cgtaacaact | ccgagtgtaa | tacaattaac   60 |
| gcctgatgat | agagtaacgc | ctgatgataa | aggtgaatat | caacccgttg | aaaagcaaat  120 |
| agcgggagat | ataatacgtg | tactagaatt | caagcaaaca | aatgaaagtc | atacaggatt  180 |
| gtatggaatt | gcatatcgag | ctaagaaagt | aataatagca | tatgctttag | cggtaagtgg  240 |
| tattcataat | gtctctcaac | ttccagaaga | ctattataaa | aataaggata | acacaggtag  300 |
| aatttatcaa | gaatacatgt | ctaatctttt | atctgcacta | ttgggtgaga | atggtgatca  360 |
| aatttctaaa | gatatggcaa | atgattttac | ccagaacgaa | ctggagtttg | gaggtcaacg  420 |
| tcttaaaaat | acctgggata | ttcctgatct | tgagaataaa | ctattggaag | attattcaga  480 |
| tgaagataaa | ttattagcac | tatatttctt | tgcttcacaa | gaacttccaa | tggaggcaaa  540 |
| tcaacaatca | aatgcagcaa | attttttttaa | agtaattgat | tttttactta | tcttatctgc  600 |
| tgtaacatca | ctgggaaaaa | ggattttttc | aaaaaatttt | tacaatggtc | tagaaactaa  660 |
| atcattagag | aattatattg | agagaaaaaa | actttctaaa | cctttctttc | gaccaccgca  720 |
| gaagttacct | gatggcagaa | caggctactt | ggccggtcca | acaaaagcgc | ctaaattgcc  780 |
| aacaacgtct | tctacagcaa | caacgtctac | agcagcttca | tctaattgga | gagttagttt  840 |
| gcaaaaactt | agagataacc | catccagaaa | tacatttatg | aaaatggatg | atgctgcaaa  900 |
| acgaaaatat | agttcatttta | taaagaggt | acaaaagggt | aatgatccac | gtgcagcagc  960 |
| agcaagtatt | ggtacaaaaa | gcggcagtaa | cttcgaaaaa | ctgcaaggta | gagatttata 1020 |
| tagtataaga | ctaagccaag | aacacagggt | aacattctcc | ataaataata | ctgaccaaat 1080 |
| aatggagatc | caaagtgttg | gaactcatta | ccaaaatata | taacctgatt | tatagtagtg 1140 |
| ataagacgta | agataaatat | ggaaggttgt | aattctattg | cacttcctca | gaggtgaccg 1200 |
| ctcag | | | | |             1205 |

<210> SEQ ID NO 6
<211> LENGTH: 1388
<212> TYPE: PRT
<213> ORGANISM: Photorhabdus luminescens

<400> SEQUENCE: 6

Ala Ala Gly Cys Thr Thr Gly Cys Thr Ala Ala Thr Ala Ala Thr Thr
1               5                   10                  15

Cys Thr Thr Gly Cys Gly Thr Ala Ala Gly Thr Thr Ala Ala Thr Thr
                20                  25                  30

Thr Thr Ala Cys Ala Thr Gly Ala Ala Ala Thr Ala Ala Cys
            35                  40                  45

Gly Cys Thr Thr Ala Ala Ala Ala Ala Gly Cys Cys Ala Gly Gly Gly
        50                  55                  60

Ala Ala Ala Ala Cys Thr Cys Thr Ala Thr Ala Thr Thr Ala Ala
65                  70                  75                  80

Ala Gly Thr Thr Gly Ala Ala Ala Thr Thr Thr Ala Thr Ala Thr Thr
                85                  90                  95

-continued

```
Ala Gly Thr Ala Gly Cys Gly Ala Cys Ala Ala Ala Thr Thr Gly Cys
            100                 105                 110

Gly Gly Ala Gly Thr Thr Thr Thr Cys Thr Gly Cys Cys Ala Gly Ala
        115                 120                 125

Ala Ala Thr Thr Thr Cys Ala Thr Ala Gly Cys Thr Cys Ala Ala Ala
    130                 135                 140

Thr Ala Ala Ala Cys Ala Thr Thr Ala Ala Cys Ala Thr Ala Ala Thr
145                 150                 155                 160

Gly Gly Ala Gly Ala Ala Ala Thr Ala Thr Ala Ala Thr Gly Gly Thr
                165                 170                 175

Thr Ala Thr Ala Cys Ala Ala Thr Thr Ala Ala Cys Ala Cys Cys Thr
            180                 185                 190

Gly Ala Thr Gly Ala Thr Ala Gly Ala Ala Gly Thr Gly Gly Ala Thr
        195                 200                 205

Ala Thr Cys Cys Ala Cys Cys Cys Gly Thr Thr Gly Ala Ala Ala Ala
    210                 215                 220

Gly Cys Ala Ala Ala Thr Ala Gly Cys Ala Gly Gly Ala Gly Ala Thr
225                 230                 235                 240

Ala Thr Ala Gly Thr Ala Cys Gly Thr Ala Thr Ala Cys Thr Ala Ala
                245                 250                 255

Ala Cys Thr Thr Thr Ala Ala Gly Cys Ala Ala Ala Cys Ala Gly Ala
            260                 265                 270

Thr Gly Ala Gly Gly Gly Thr Cys Ala Thr Ala Cys Ala Gly Cys Ala
        275                 280                 285

Thr Cys Ala Thr Ala Thr Gly Gly Ala Ala Thr Thr Gly Ala Ala Thr
    290                 295                 300

Ala Thr Cys Gly Ala Gly Cys Thr Ala Ala Gly Ala Ala Ala Ala Thr
305                 310                 315                 320

Ala Ala Thr Ala Thr Thr Ala Gly Cys Thr Thr Ala Cys Gly Cys Thr
                325                 330                 335

Thr Thr Gly Gly Cys Thr Gly Thr Ala Ala Gly Thr Gly Gly Thr Ala
            340                 345                 350

Thr Thr Cys Ala Thr Ala Ala Thr Gly Thr Ala Thr Cys Thr Ala Ala
        355                 360                 365

Ala Cys Thr Thr Cys Cys Thr Gly Ala Thr Gly Ala Cys Thr Ala Thr
    370                 375                 380

Thr Ala Thr Ala Ala Gly Ala Ala Thr Ala Ala Gly Ala Gly Ala
385                 390                 395                 400

Cys Thr Gly Cys Thr Gly Ala Gly Ala Gly Ala Ala Thr Thr Thr Ala
                405                 410                 415

Thr Cys Ala Ala Gly Ala Ala Thr Ala Thr Ala Thr Gly Thr Cys Thr
            420                 425                 430

Ala Ala Thr Cys Thr Thr Thr Cys Ala Thr Cys Thr Gly Cys Ala Cys
        435                 440                 445

Thr Ala Thr Thr Ala Gly Gly Thr Gly Ala Ala Ala Ala Thr Gly Gly
    450                 455                 460

Thr Gly Ala Thr Cys Ala Ala Ala Thr Thr Thr Cys Thr Ala Ala Ala
465                 470                 475                 480

Gly Ala Thr Ala Thr Gly Gly Cys Ala Ala Ala Thr Gly Gly Thr Thr
                485                 490                 495

Thr Thr Thr Ala Thr Ala Ala Gly Ala Ala Thr Gly Ala Ala Cys Thr
            500                 505                 510

Gly Gly Ala Thr Thr Thr Thr Gly Ala Ala Gly Gly Thr Cys Ala Ala
```

-continued

```
            515                 520                 525

Thr Ala Thr Cys Cys Thr Cys Ala Ala Ala Cys Ala Thr Thr Thr
            530                 535                 540

Gly Gly Ala Ala Thr Gly Thr Thr Cys Cys Thr Gly Ala Gly Cys Thr
545                 550                 555                 560

Thr Gly Ala Ala Ala Ala Thr Ala Ala Ala Cys Cys Ala Thr Thr Gly
                565                 570                 575

Ala Gly Thr Gly Cys Thr Thr Ala Thr Thr Cys Ala Gly Ala Thr Gly
                580                 585                 590

Ala Cys Gly Ala Thr Ala Ala Ala Thr Thr Ala Thr Thr Ala Gly Cys
                595                 600                 605

Ala Cys Thr Ala Thr Ala Thr Thr Thr Thr Thr Cys Thr Cys Thr
            610                 615                 620

Gly Thr Ala Cys Ala Gly Gly Ala Ala Ala Thr Thr Cys Cys Ala Cys
625                 630                 635                 640

Thr Gly Gly Ala Gly Gly Ala Ala Ala Thr Cys Ala Ala Cys Ala
                645                 650                 655

Ala Thr Cys Ala Ala Ala Thr Gly Cys Cys Gly Cys Ala Ala Gly Ala
            660                 665                 670

Thr Thr Thr Thr Thr Thr Ala Ala Ala Thr Thr Ala Ala Thr Thr Gly
            675                 680                 685

Ala Thr Thr Thr Cys Thr Thr Ala Thr Thr Thr Ala Cys Cys Thr Thr
            690                 695                 700

Ala Thr Cys Thr Gly Cys Thr Gly Thr Ala Ala Cys Thr Thr Cys Ala
705                 710                 715                 720

Cys Thr Gly Gly Gly Ala Ala Gly Gly Ala Gly Gly Ala Thr Thr Thr
                725                 730                 735

Thr Thr Thr Cys Ala Ala Ala Ala Ala Ala Cys Thr Thr Thr Thr Ala
            740                 745                 750

Cys Ala Ala Thr Gly Gly Ala Thr Thr Ala Gly Ala Gly Gly Cys Thr
            755                 760                 765

Ala Ala Ala Thr Cys Ala Thr Thr Ala Gly Ala Gly Ala Ala Thr Thr
            770                 775                 780

Ala Thr Ala Thr Gly Ala Gly Ala Gly Ala Ala Ala Ala Ala Ala
785                 790                 795                 800

Ala Cys Thr Thr Thr Cys Thr Ala Ala Cys Cys Thr Thr Thr Cys
                805                 810                 815

Thr Thr Thr Cys Gly Ala Cys Cys Ala Cys Cys Gly Cys Ala Gly Ala
            820                 825                 830

Gly Ala Thr Thr Ala Cys Cys Thr Gly Ala Thr Gly Gly Cys Ala Gly
            835                 840                 845

Ala Ala Thr Ala Gly Gly Thr Thr Ala Thr Thr Gly Gly Cys Thr
850                 855                 860

Gly Gly Ala Cys Cys Ala Ala Cys Ala Gly Ala Ala Gly Cys Gly Cys
865                 870                 875                 880

Cys Thr Ala Ala Ala Thr Gly Gly Ala Gly Ala Gly Thr Gly Ala Gly
                885                 890                 895

Thr Thr Thr Thr Ala Ala Ala Gly Ala Ala Cys Thr Thr Ala Ala Ala
            900                 905                 910

Ala Ala Thr Ala Ala Cys Ala Ala Thr Cys Thr Ala Gly Gly Ala
            915                 920                 925

Ala Thr Gly Gly Ala Thr Thr Thr Cys Thr Ala Ala Thr Ala Thr
            930                 935                 940
```

Gly Gly Ala Ala Gly Gly Gly Cys Thr Gly Cys Ala Ala Ala
945             950             955             960

Cys Ala Ala Ala Ala Gly Thr Ala Thr Ala Gly Thr Thr Cys Ala Thr
            965             970             975

Thr Thr Ala Thr Ala Ala Ala Ala Gly Ala Gly Gly Thr Ala Cys Ala
        980             985             990

Ala Ala Ala Gly Gly Gly Thr Ala Ala Cys Gly Cys Thr Cys Cys Ala
        995             1000            1005

Cys Ala Gly Ala Cys Ala Gly Cys Ala Gly Cys Gly Ala Ala Ala
    1010            1015            1020

Ala Gly Thr Ala Thr Thr Gly Gly Thr Ala Cys Ala Gly Cys Cys
    1025            1030            1035

Ala Gly Thr Gly Gly Cys Ala Gly Thr Ala Ala Cys Cys Thr Gly
    1040            1045            1050

Gly Ala Ala Ala Ala Thr Thr Gly Cys Cys Gly Ala Ala Thr
    1055            1060            1065

Ala Ala Thr Thr Thr Ala Thr Ala Thr Ala Gly Thr Gly Thr Gly
    1070            1075            1080

Ala Gly Gly Cys Thr Ala Ala Gly Cys Cys Ala Ala Ala Ala
    1085            1090            1095

Gly Ala Cys Ala Gly Gly Gly Thr Ala Ala Cys Cys Thr Thr Thr
    1100            1105            1110

Ala Cys Thr Cys Ala Ala Ala Ala Thr Gly Ala Thr Ala Cys Thr
    1115            1120            1125

Gly Ala Cys Ala Ala Thr Ala Cys Ala Ala Thr Gly Ala Cys Gly
    1130            1135            1140

Gly Thr Thr Cys Ala Thr Ala Gly Thr Gly Thr Thr Gly Gly Ala
    1145            1150            1155

Ala Cys Thr Cys Ala Thr Thr Ala Thr Ala Ala Ala Ala Ala Thr
    1160            1165            1170

Ala Thr Ala Thr Gly Ala Thr Gly Ala Gly Thr Ala Ala Thr Cys
    1175            1180            1185

Thr Cys Thr Gly Ala Cys Thr Thr Cys Gly Ala Thr Thr Gly Ala
    1190            1195            1200

Cys Ala Gly Ala Gly Cys Ala Thr Thr Thr Thr Ala Ala Gly
    1205            1210            1215

Cys Thr Cys Thr Cys Ala Thr Thr Thr Thr Cys Thr Cys Ala Ala
    1220            1225            1230

Cys Gly Gly Gly Ala Gly Thr Cys Thr Cys Ala Thr Ala Ala Gly
    1235            1240            1245

Gly Cys Gly Thr Thr Thr Thr Ala Cys Thr Thr Thr Cys Ala
    1250            1255            1260

Ala Gly Cys Cys Ala Cys Thr Ala Thr Gly Thr Gly Gly Thr Cys
    1265            1270            1275

Thr Gly Thr Gly Ala Thr Ala Ala Thr Thr Gly Thr Ala Ala Ala
    1280            1285            1290

Ala Cys Gly Cys Cys Thr Thr Cys Thr Thr Thr Thr Ala Gly Cys
    1295            1300            1305

Cys Ala Ala Thr Ala Cys Ala Cys Thr Thr Thr Ala Cys Thr Ala
    1310            1315            1320

Cys Cys Ala Ala Gly Ala Ala Ala Ala Thr Ala Thr Ala Thr Ala
    1325            1330            1335

```
Cys Cys Cys Thr Ala Thr Gly Gly Ala Thr Thr Thr Cys Ala Ala
        1340            1345                1350

Gly Ala Thr Gly Gly Ala Thr Cys Gly Cys Gly Cys Gly Gly
        1355            1360                1365

Cys Ala Ala Gly Gly Gly Ala Gly Cys Gly Ala Ala Thr Cys Cys
        1370            1375                1380

Cys Cys Gly Gly Gly
        1385
```

<210> SEQ ID NO 7
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 7
ttagcggtaa gtggtattca t                                      21

<210> SEQ ID NO 8
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 8
aggcaaatca acaatcaaat g                                      21

<210> SEQ ID NO 9
<211> LENGTH: 20
<212> TYPE: DNA
<213> ORGANISM: Artificial Sequence
<220> FEATURE:
<223> OTHER INFORMATION: Derived from X. nematophilus

<400> SEQUENCE: 9
gacgtaaact aacaactaaa                                        20

<210> SEQ ID NO 10
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 10
tgatggcaga acaggctact t                                      21

<210> SEQ ID NO 11
<211> LENGTH: 21
<212> TYPE: DNA
<213> ORGANISM: Artificial Sequence
<220> FEATURE:
<223> OTHER INFORMATION: Derived from X. nematophilus

<400> SEQUENCE: 11
tctgcaacaa cgacatcttc t                                      21

<210> SEQ ID NO 12
<211> LENGTH: 20
<212> TYPE: DNA
<213> ORGANISM: Artificial Sequence
<220> FEATURE:
<223> OTHER INFORMATION: Derived from X. nematophilus

<400> SEQUENCE: 12
ggacacaaga accgaatcag                                               20

<210> SEQ ID NO 13
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 13
atggtgaatg tcggtttcgc                                               20

<210> SEQ ID NO 14
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 14
tgaactggat tttgaaggtc                                               20

<210> SEQ ID NO 15
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 15
gcagtagact tattcgtgag                                               20

<210> SEQ ID NO 16
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 16
ctttcgacca ccgcagagat                                               20

<210> SEQ ID NO 17
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 17
gtaaatccgc gaagacaacc                                               20

<210> SEQ ID NO 18
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 18
tgacggttca tagtgttgga                                               20

<210> SEQ ID NO 19

```
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 19
aggttgtgat acttggcagt                                           20

<210> SEQ ID NO 20
<211> LENGTH: 20
<212> TYPE: DNA
<213> ORGANISM: Artificial Sequence
<220> FEATURE:
<223> OTHER INFORMATION: Derived from P. luminescens

<400> SEQUENCE: 20
ccatcatttc acataaccga                                           20
```